US009550803B2

(12) United States Patent
McKenna et al.

(10) Patent No.: US 9,550,803 B2
(45) Date of Patent: Jan. 24, 2017

(54) METHOD TO IMPROVE ANTIVIRAL ACTIVITY OF NUCLEOTIDE ANALOGUE DRUGS

(75) Inventors: Charles E. McKenna, Pacific Palisades, CA (US); Boris A Kashemirov, Los Angeles, CA (US); Ivan S Krylov, Los Angeles, CA (US); Valeria M. Zakharova, Mannheim (DE)

(73) Assignee: University of Southern California, Los Angeles, CA (US)

( * ) Notice: Subject to any disclaimer, the term of this patent is extended or adjusted under 35 U.S.C. 154(b) by 99 days.

(21) Appl. No.: 14/114,827

(22) PCT Filed: May 7, 2012

(86) PCT No.: PCT/US2012/036846
§ 371 (c)(1),
(2), (4) Date: Dec. 19, 2013

(87) PCT Pub. No.: WO2012/154698
PCT Pub. Date: Nov. 15, 2012

(65) Prior Publication Data
US 2014/0100186 A1 Apr. 10, 2014

Related U.S. Application Data

(60) Provisional application No. 61/483,534, filed on May 6, 2011.

(51) Int. Cl.
| | | |
|---|---|---|
| *C12N 5/00* | (2006.01) |
| *C12N 5/02* | (2006.01) |
| *A01N 43/04* | (2006.01) |
| *A61K 31/70* | (2006.01) |
| *C07H 19/20* | (2006.01) |
| *C07H 19/04* | (2006.01) |
| *C07H 19/10* | (2006.01) |
| *C07H 19/048* | (2006.01) |
| *C07H 19/23* | (2006.01) |
| *A61K 47/48* | (2006.01) |

(52) U.S. Cl.
CPC ......... *C07H 19/23* (2013.01); *A61K 47/48038* (2013.01); *A61K 47/48253* (2013.01); *C07H 19/10* (2013.01); *C07H 19/20* (2013.01)

(58) Field of Classification Search
CPC .............. A61K 47/48038; A61K 47/48253; C07H 19/23; C07H 19/20; C07H 19/10
See application file for complete search history.

(56) References Cited

U.S. PATENT DOCUMENTS

| 4,199,574 A * | 4/1980 | Schaeffer ............... 514/81 |
| 4,355,032 A * | 10/1982 | Verheyden et al. ...... 514/263.38 |
| 4,808,716 A * | 2/1989 | Holy et al. ............... 544/244 |
| 6,037,335 A | 3/2000 | Takashima et al. |
| 7,193,081 B2 | 3/2007 | Kopcho et al. |
| 7,214,668 B2 | 5/2007 | Reddy et al. |
| 7,511,051 B2 | 3/2009 | McKenna et al. |
| 8,063,209 B2 | 11/2011 | Hilfinger et al. |
| 8,940,313 B2 * | 1/2015 | McKenna et al. ............ 424/402 |
| 2006/0246130 A1 | 11/2006 | Dahl et al. |
| 2007/0003608 A1 | 1/2007 | Almond et al. |
| 2008/0227754 A1 | 9/2008 | Becker et al. |
| 2009/0270618 A1 | 10/2009 | Hilfinger et al. |
| 2010/0081628 A1 | 4/2010 | Du et al. |
| 2011/0263535 A1 | 10/2011 | McKenna |

OTHER PUBLICATIONS

Shoshani et al., "Inhibition of Adenyl Cyclase by Acyclic Nucleoside Phosphate Antiviral Agents," Journal of Biological Chemistry, 274(49), 34742-34744 (Dec. 3, 1999).*
Pertusati et al., "Medicinal Chemistry of Nucleoside Phosphonate Prodrugs for Antiviral Therapy," Antiviral Chemistry & Chemotherapy, 22(5), 181-203 (May 2012).*
PCT Search Report and Written Opinion dated Jan. 19, 2012 and issued in connection with related PCT/US2011/033703.
Peterson, L., et al, "Serine side chain-linked peptidomimetic conjugates of cyclic HPMPC and HPMPA: synthesis and interaction with hPEPT1" Mol Pharm, epub Oct. 7, 2010 vol. 7, No. 6, pp. 2349-2361.
De Clercq, E., The acyclic nucleoside phosphonates from inception to clinical use: historical perspective, Antiviral Res. 2007, 1-13.
Clercq, E. D.; Holy, A.; Rosenberg, I.; Sakuma, T.; Balzarini, J.; Maudgal, P. C. A novel selective broad-spectrum anti-DNA virus agent. Nature 1986, 323, 464-467.
Clercq, E. D., Sakuma, T.; Baba, M.; Pauwels, R.; Balzarini, J.; Rosenberg, I.; Holy, A. Antiviral activity of phosphonylmethoxyalkyl derivatives of purine and pyrimidines. Antiviral Research 1987, 8, 261-272.
Cundy, K. C.; Bidgood, A. M.; Lynch, G.; Shaw, J. P.; Griffin, L.; Lee, W. A. Pharmacokinetics, bioavailability, metabolism, and tissue distribution of cidofovir (HPMPC) and cyclic HPMPC in rats. Drug Metabolism and Disposition 1996, 24, 745-752.

(Continued)

Primary Examiner — Lawrence E Crane
(74) Attorney, Agent, or Firm — Berliner & Associates

(57) ABSTRACT

An amino acid conjugate of a cyclic or acyclic nucleoside phosphonate is provided. In some cases, the amino acid conjugate is a tyrosine alkyl amide phosphonate ester conjugate of a cyclic or acyclic nucleoside phosphonate, and is useful as an antiviral compound. In certain cases, the tyrosine conjugate includes a long chain alkyl group on the carboxamide group of the tyrosine residue. In a method of preparing an acyclic tyrosine conjugate, a tert-butyloxycarbonyl (Boc) protected tyrosine residue containing a long chain alkyl group is reacted with an acyclic nucleoside phosphonate mono-ethyl ester in the presence of benzotriazol-1-yl-oxytripyrrolidinophosphonium hexafluorophosphate to produce a Boc-protected nucleoside phosphonate di-ester, and the di-ester is deethylated and deprotected to produce the tyrosine conjugate. Methods of inhibiting viral replication and methods of treating a viral infection using the amino acid conjugate are also provided.

18 Claims, 1 Drawing Sheet

(56) References Cited

OTHER PUBLICATIONS

Bijsterbosch MK, S. L., van Berkel TJ. Disposition of the acyclic nucleoside phosphonate (S)-9-(3-hydroxy-2-phosphonylmethoxypropyl)adenine. Antimicrob Agents Chemother. 1998 1998, 42, 1146-50.

Cundy KC, L. Z., Hitchcock MJ, Lee WA. Pharmacokinetics of cidofovir in monkeys. Evidence for a prolonged elimination phase representing phosphorylated drug. Drug Metab Dispos. 1996, 24, 738-44.

Peterson, L. W., McKenna, C. E. Prodrug approaches to improving the oral absorption of antiviral nucleotide analogues. Expert Opinion on Drug Delivery 2009, 6, 405-420.

Eriksson, U.; Peterson, L. W.; Kashemirav, B. A.; Hilfinger, J. M.; Drach, J. C.; Borysko, K. Z.; Breitenbach, J. M.; Kim, J. S.; Mitchell, S.; Kijek, P.; McKenna, C. E. Serine Peptide Phosphoester Prodrugs of Cyclic Cidofovir: Synthesis, Transport, and Antiviral Activity. Molecular Pharmaceutics 2008, 5, 598-609.

Kikuchi, C.; Nagaso, H.; Hiranuma, T.; Koyama, M. Tetrahydrobenzindoles: Selective Antagonists of the 5-HT7 Receptor. Journal of Medicinal Chemistry 1999, 42, 533-535.

Grimm, J. B.; Wilson, K. J.; Witter, D. J. Suppression of racemization in the carbonylation of amino acid-derived aryl triflates. Tetrahedron Letters 2007, 48, 4509-4513.

Miyazawa T., H. S., Tsuboi Y., Yamada T., Kuwata S. Studies of unusual amino acids and their peptides. XVII. The synthesis of peptides containing N-carboxymethyl amino acids. II. Bull. Chem. Soc. Jpn. 1985, 58, 1976-82.

Cornish, J.; Callon, K. E.; Lin, C. Q. X.; Xiao, C. L.; Mulvey. T. B.; Cooper, G. J. S.; Reid, I. R. Trifluoroacetate, a contaminant in purified proteins, inhibits proliferation of osteoblasts and chondrocytes. Am J Physiol Endocrinol Metab 1999, 277, E779-783.

De Clercq E, Neyts, Therapeutic potential of nucleoside/nucleotide analogues against poxvirus infections, J Rev Med Virol. Sep.-Oct. 2004;14(5):289-300.

Turk, S. R.; Shipman, C., Jr.; Nassiri, R.; Genzlinger, G.; Krawczyk, S. H.; Townsend, L. B.; Drach, J. C. Pyrrolo[2,3-d] pyrimidine nucleosides as inhibitors of human cytomegalovirus. Antimicrob. Agents Chemother. 1987, 31, 544-550.

Prichard, M. N.; Turk, S. R.; Coleman, L. A.; Engelhardt, S. L.; Shipman, C., Jr.; Drach, J. C. A microtiter virus yield reduction assay for the evaluation of antiviral compounds against human cytomegalovirus and herpes simplex virus. J. Virol. Methods 1990, 28, 101-106.

Kern, E. R.; Hartline, C.; Harden, E.; Keith, K.; Rodriguez, N.; Beadle, J. R.; Hostetler, K. Y. Enhanced inhibition of orthopoxvirus replication in vitro by alkoxyalkyl esters of cidofovir and cyclic cidofovir. Antimicrob. Agents Chemother. 2002, 46, 991-995.

Office Action dated Mar. 7, 2014 issued in connection with related U.S. Appl. No. 13/092,939, filed Apr. 23, 2011.

PCT Search Report and Written Opinion issued Nov. 29, 2012 in connection with related PCT/US2012/036846.

\* cited by examiner

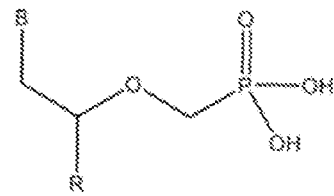 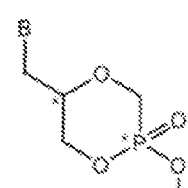 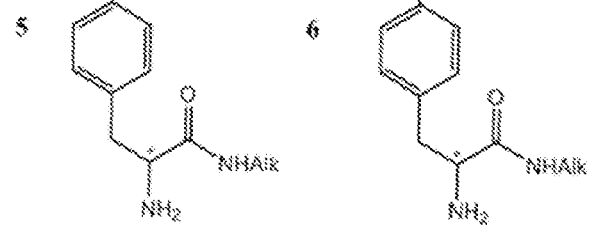

1  (S)-HPMPA, B = A, R = CH$_2$OH
2  (S)-HPMPC, B = C, R = CH$_2$OH
3  PMEA, B = A, R = H
4  (R)-PMPDAP, B = DAP, R = CH$_3$
1a  (S)-FPMPA, B = A, R = CH$_2$F
1b  (S)-FPMPDAP, B = DAP, R = CH$_2$F
1c  (S)-FPMPG, B = G, R = CH$_2$F
1d  (R)-FPMPDAP, B = DAP, R = CH$_2$F
1e  (R)-FPMPG, B = G, R = CH$_2$F
1f  7-deaza-PMEG, B= 7-deaza-G, R = H
1g  PME-8-aza-G, B = 8-aza-G, R = H
1h  (R)-PMP-8-aza-G, B = 8-aza-G, R = CH$_3$
1i  PMEO-DAPy, B = DAPy, R = H
1j  (R)-PMPO-DAPy, B = DAPy, R = CH$_3$

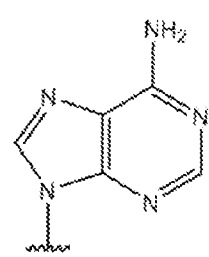 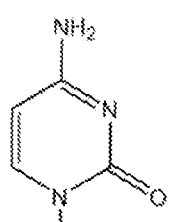 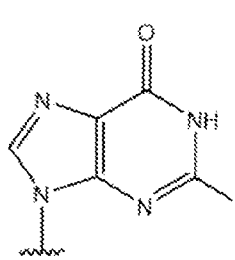 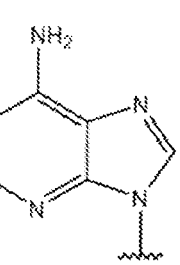

9-Adeninyl (A)   1-Cytosinyl (C)   9-Guaninyl (G)   2,6-Diamino-9-purinyl (DAP)

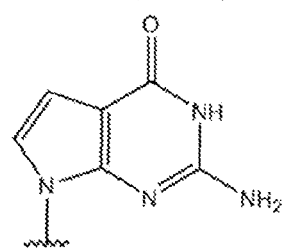 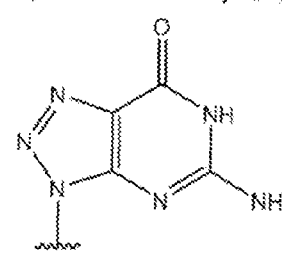 

7-Deaza-9-guaninyl  8-Aza-9-guaninyl  2,4-Diaminopyrimidine-6-oxidanyl
(7-deaza-G)         (8-aza-G)         (DAPy)

METHOD TO IMPROVE ANTIVIRAL ACTIVITY OF NUCLEOTIDE ANALOGUE DRUGS

CROSS-REFERENCE TO RELATED APPLICATIONS

This application is the National Stage of International Application No. PCT/US2012/036,846, filed on May 7, 2012, which claims the benefit of Provisional Patent Application No. 61/483,534, filed on May 6, 2011, which is incorporated by reference herein.

STATEMENT REGARDING FEDERALLY SPONSORED RESEARCH OR DEVELOPMENT

This invention was made with Government support under Grant Nos. R43AI091216 and R44AI056864 from the National Institutes of Health. The Government has certain rights in this invention.

BACKGROUND

Field of Invention

The invention relates to antiviral compounds and methods of their preparation.

Related Art

Acyclic nucleoside phosphonates (ANPs) are broad spectrum antiviral agents that are highly potent against orthopox viruses, including cowpox, vaccinia, and variola (smallpox) virus [1]. The prototype member of the ANPs is (S)-9-(3hydroxy-2-phosphonyl-methoxypropyl)adenine ((S)-HPMPA, 1, see FIG. 1), first described 1986 for its activity against DNA viruses [2]. Its cytosine analogue, (S)-HPMPC (cidofovir, 2, see FIG. 1) [3] has been shown to have similar therapeutic potential against virtually all DNA viruses as well as other adeno-, papiloma-, polyoma-, and poxvirus infections. Cidofovir is used in the clinic for the treatment of AIDS patients infected with cytomegalovirus (CMV).

(S)-HPMPC is effective in vitro and in animal model infections but has low oral bioavailability, and must be delivered intravenously [4]. This condition limits the therapeutic scope of this and other ANP drugs. Moreover, after intravenous injection drugs of this class tend to accumulate in the kidney leading to renal toxicity [5,6]. Thus, there is a need for more effective, orally bioavailable forms of these drugs.

Several prodrug approaches to improve oral absorption of antiviral nucleoside analogues by incorporating various phosphonate anion masking groups have been developed [7].

SUMMARY

The inventors have previously described the installation of a benign promoiety, such as single amino acid, dipeptide, or tripeptide containing a side chain hydroxy for esterification of the nucleotide phosphonic acid [8]. As described in the present application, tyrosine alkyl amide phosphonate ester conjugates of nucleotide drugs in which the amidoalkyl chain is longer than 5 carbon atoms and less than 19 carbon atoms, and in embodiments of 8, 12 or 16 carbon atoms, have greatly increased potency.

In one aspect, a method of increasing the antiviral activity of a compound is provided. The method involves modifying a nucleotide or a nucleotide analogue to increase its overall effectiveness in treating an antiviral disease. The nucleotide or nucleotide analogue may be a nucleotide drug, and particularly an antiviral nucleotide drug. In particular embodiments, the nucleotide analogue may be a phosphonate analogue of a nucleotide having a naturally-occurring base or an unnatural base. In some embodiments, the phosphonate analogue can be a nucleoside monophosphonate analogue. The modification may comprise adding a lipophilic $C_6$ or greater alkyl group to the nucleotide, nucleotide analogue, or phosphonate analogue. In embodiments where a lipophilic $C_6$ or greater alkyl group is added, a linking group between the nucleotide phosphonate analogue and alkyl group can be an amino acid residue or a peptide, including a dipeptide.

In some embodiments, the following can be included: (a) The method comprises adding the lipophilic $C_6$ or greater alkyl group to a carboxamide functional group of an amino acid residue or a peptide, where the residue or peptide is attached via an alcoholic side-chain to a phosphonate analogue of a nucleotide having a naturally-occurring base or an unnatural base. Thus, the amino acid residue or peptide, including a dipeptide, is a linking group between the lipophilic alkyl group and the phosphonate analogue, and links the lipophilic alkyl group to the phosphonate analogue. (b) In some embodiments, including the embodiments in (a), the amino acid residue can be a tyrosine, serine or threonine residue, or a derivative thereof. (c) In some embodiments, including the embodiments in (a) or (b), antiviral activity can be improved by 10-fold or more compared to the unmodified compound. (d) In some embodiments, including the embodiments in (a), (b) or (c), the base can be adenine, cytosine, guanine, 2,6-diaminopurine, or 2,4-diaminopyrimidine.

In another aspect, any compound prepared by the modifying method, or a salt thereof, especially a compound having antiviral activity, is provided. The compound can be of the formula: base-sugar-A-X, or a salt thereof. In the formula, the base-sugar is a cyclic or acyclic sugar analogue of a nucleoside or an analogue thereof, A is a phosphonate moiety, and X is an amino acid residue or derivative thereof, or a dipeptide or derivative thereof. X comprises a side-chain oxygen which is connected to the phosphonate moiety by an ester linkage.

In some embodiments, the following can be included: (a) X can be a serine, threonine or tyrosine residue or derivative thereof (b) X can be a dipeptide or a derivative thereof, and may comprise a serine, threonine or tyrosine residue or derivative thereof, or a combination thereof with amino acids or derivatives thereof (c) In some embodiments, including the embodiments in (a) or (b), X comprises a lipophilic $C_6$ or greater alkyl group, which may be attached to an amide group of X. In some of these embodiments, a single lipophilic $C_6$ or greater alkyl group is attached. The amide group may be a carboxamide group of the amino acid residue, dipeptide, or derivative thereof. Thus, X may comprise an alkylamido group comprising a $C_6$ or greater alkyl group. (d) In some embodiments, including the embodiments in (a), (b) or (c), X is a tyrosine residue or derivative thereof, and may comprise a carboxamide group NRR', where R=H and R'=a $C_{8-18}$ alkyl group. (e) In some embodiments, including the embodiments in (a), (b), (c) or (d), the base-sugar may be a base-sugar analogue portion of a cyclic or acyclic sugar analogue of a nucleotide or nucleotide analogue that has antiviral activity. Thus, the base-sugar may be, for example, the base-sugar analogue portion of HPMPA, cyclic HPMPA, HPMPC, cyclic HPMPC, or any compound shown in FIG. 1, Schemes 1-3, or Table 1. (f) In some embodiments, including the embodiments in (a), (b), (c), (d) or (e), the base can be a naturally occurring or unnatural base, and can be adenine, cytosine or 2,6-diaminopurine.

In some embodiments, the compound has the formula (I) or (II)

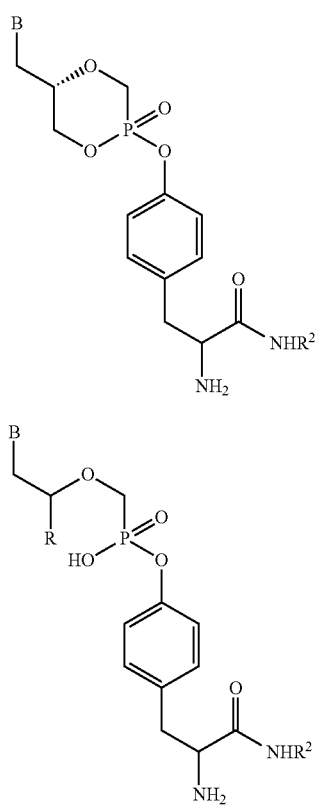

where B is a naturally occurring or unnatural base, R is H, $CH_2OH$ or methyl, and $R^2$ is a $C_6$ or greater alkyl group. In some embodiments, B can be adenine, cytosine, guanine, 2,6-diaminopurine or 2,4-diaminopyrimidine. In some embodiments, the compound is (L)-Tyr (NHC$_8$H$_{17}$)—(S)-cHPMPA, (L)-Tyr(NHC$_{12}$H$_{25}$)—(S)-cHPMPA, (L)-Tyr (NHC$_{16}$H$_{33}$)—(S)-cHPMPA, (L)-Tyr(NHC$_8$H$_{17}$)—(S)-HPMPA, (L)-Tyr(NHC$_{12}$H$_{25}$)—(S)-HPMPA (L)-Tyr (NHC$_{16}$H$_{33}$)—(S)-HPMPA, (L)-Tyr(NHC$_8$H$_{17}$)-PMEA, (L)-Tyr(NHC$_{16}$H$_{33}$)-PMEA, or (L)-Tyr (NHC$_8$H$_{17}$)—(R)-PMPDAP.

In a further aspect, a method of preparing a phosphonate analogue of an acyclic sugar analogue of a nucleotide is provided. The method comprises: reacting a nucleoside phosphonate with EtOH in the presence of bromotripyrrolidinophosphonium hexafluorophosphate (PyBrOP) to produce a nucleoside phosphonate mono-ethyl ester; coupling the nucleoside phosphonate mono-ethyl ester to a Boc-protected amino acid, where the Boc-protected amino acid comprises a carboxamide group containing a $C_6$ or greater alkyl moiety, to produce a Boc-protected nucleoside phosphonate di-ester; and de-ethylating and deprotecting the Boc-protected nucleoside phosphonate di-ester to produce a phosphonate analogue. The nucleoside phosphonate can be an adenine or 2,6-diaminopurine nucleoside phosphonate. The Boc-protected amino acid can be a Boc-protected tyrosine derivative.

In addition, a compound prepared by the modifying method may be any compound shown in FIG. 1, Schemes 1-3, or Table 1, or a salt thereof. Further, the compound may be a cyclic or acyclic antiviral compound.

In a version of the modifying method, the method may be applied to foscarnet by modifying the phosphonate moiety of the compound.

In a further aspect, a pharmaceutical composition comprising any antiviral compound or a salt thereof prepared by the modifying method, or described herein, is provided. Also provided is a method of inhibiting viral replication in a virus-infected cell by exposing the cell to any antiviral compound or a salt thereof prepared by the modifying method or described herein. In addition, a method of treating a viral infection in an individual, comprising administering to the individual a therapeutically effective amount of any antiviral compound or a salt thereof prepared by the modifying method or described herein is provided.

BRIEF DESCRIPTION OF THE DRAWINGS

For a more complete understanding of the present invention, reference is now made to the following descriptions taken in conjunction with the accompanying drawings, in which:

FIG. 1 is a drawing of nucleoside phosphonates.

DETAILED DESCRIPTION

In embodiments, the nucleotide, nucleotide analogue, or phosphonate analogue of a nucleotide or nucleotide analogue may comprise a naturally occurring base or an unnatural base. Naturally-occurring bases include adenine, cytosine, guanine, uracil and thymine; unnatural bases include, but are not limited to, 2,6-diaminopurine, 8-azaadenine, 2,4-diaminopyrimidine, 5-azacytosine, 7-deazaadenine, and 7-deazaguanine.

In embodiments comprising a lipophilic $C_6$ or greater alkyl group, the alkyl group may be linear or branched. In particular embodiments, the alkyl group may be a $C_{6-20}$ alkyl, $C_{6-18}$ alkyl, $C_{8-16}$ alkyl, or $C_{8-18}$ alkyl group.

The term "amino acid residue" means an amino acid lacking a portion of its structure due to, for instance, attachment of the amino acid to a nucleoside or a phosphonate moiety. Examples include an amino acid residue without the OH portion of the amino acid α-carboxyl group, or lacking the H portion of the α-amino group. Also included within the definition of an amino acid residue is an amino acid lacking a portion of its side chain, such as a tyrosine amino acid lacking the H portion of the side chain —OH group.

A derivative of an amino acid residue is an amino acid residue having a portion of its structure substituted by an atom or molecular group. Examples of such derivatives include, but are not limited to, ester derivatives having an —OR group substituting for the α-carboxyl-OH group, where R is an alkyl or alkenyl group, and amide derivatives having an —NHR group substituting for the α-carboxyl-OH group. In some embodiments, R is an alkyl or alkenyl group. A dipeptide derivative is a peptide that contains two amino acid residues.

An amino acid residue may be based on any one of the twenty common amino acids found in naturally synthesized proteins. In some embodiments, the residue provides for oral bioavailability of the compounds described herein. The residue may also be based on a modified or unusual amino acid. Examples of modified or unusual amino acids include, but are not limited to, 2-aminoadipic acid, 3-aminoadipic acid, β-alanine, 2-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, N-methylglycine, N-methylisoleucine, N-methylvaline, norvaline, norleucine, ornithine and homoserine.

Both the (D) and (L) stereoisomers of an amino acid residue may be incorporated into the antiviral compounds described herein, or salts thereof. When the configuration is not designated, the amino acid or residue can have the configuration (D), (L) or (DL). For the purposes of this application, unless expressly noted to the contrary, a named amino acid shall be construed to include both the (D) or (L) stereoisomers. In some embodiments, the D configuration is selected, or in other embodiments, the L configuration is selected, or a racemic mixture of both configurations is selected.

In cases where the incorporation of one or more amino acids leads to stereoisomeric forms of a compound, the present application contemplates all such forms of the compound, including cis- and trans-isomers, R- and S-enantiomers, diastereomers, the racemic mixtures thereof, and other mixtures thereof, as falling within the scope of the application. Additional asymmetric carbon atoms may be present in a substituent such as an alkyl group. All such isomers, as well as mixtures thereof, are intended to be included in the application. Some embodiments are individual isomeric forms of a compound, which can be isolated for example by high performance liquid chromatography (HPLC).

In embodiments where a peptide is attached to a phosphonate analogue or a phosphonate moiety, the peptide can be, but not limited to, Tyr-Gly, Tyr-Ala, Tyr-Val, Tyr-Phe, Tyr-Leu, Tyr-Ile, Ser-Gly, Ser-Ala, Ser-Val, Ser-Phe, Ser-Leu, Ser-Ile, Thr-Gly, Thr-Ala, Thr-Val, Thr-Phe, Thr-Leu, Thr-Ile. Preferred peptides are Ser-Ala, Ser-Val, Ser-Phe, Tyr-Val.

In embodiments comprising an antiviral nucleotide, or the base-sugar analogue portion or base of a cyclic or acyclic sugar analogue of a nucleotide or nucleotide analogue that has antiviral activity, examples of antiviral nucleotides or nucleotide analogues include, but are not limited to, (S)-HPMPC, (S)-cHPMPC, (S)-HPMPA, (S)-cHPMPC, PMEA, (R)-PMPDAP, (S)-FPMPA, (S)-FPMDAP, (S)-FMPG, (R)-FPMDAP, (R)-FPMPG, (R)-FPMDAP, PMEO-DAPy, (R)-PMPO-DAPy, 7-deaza-PMEG, PME-8-aza-G, (R)-PMP-8-azaG (see, FIG. 1).

Antiviral compounds can be prepared as a salt, which may be a pharmaceutically acceptable salt. Pharmaceutically acceptable salts are well known in the art and include salts prepared from pharmaceutically acceptable non-toxic acids, including inorganic acids and organic acids. Suitable nontoxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic acids, and the like. Salts formed with, for example, a POH group, can be derived from inorganic bases including, but not limited to, sodium, potassium, ammonium, calcium or ferric hydroxides, and organic bases including, but not limited to, isopropylamine, trimethylamine, histidine, and procaine.

In embodiments that include a pharmaceutical composition, the composition may comprise a therapeutically effective amount of an antiviral compound, or a salt or pharmaceutically acceptable salt thereof. A therapeutically effective amount of a compound is an amount that results in an improvement or a desired change in condition for which the compound is administered, when the compound is administered once or over a period of time. For example, with respect to virus infections, the improvement can be a lowering of virus titer, or a reduction in the symptoms or discomfort associated with a viral infection. As is known, the amount will vary depending on such particulars as the type of virus infection, the condition being treated, the specific cidofovir compound utilized, the severity of the condition, and the characteristics of the patient.

The pharmaceutical composition will typically contain a pharmaceutically acceptable carrier. Although oral administration is a desired route of administration, other means of administration such as nasal, topical (for example, administration to the skin or eye) or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, drops, ointments, creams or lotions, preferably in unit dosage form suitable for single administration of a precise dosage. The compositions may include an effective amount of a selected compound in combination with a pharmaceutically acceptable carrier and, in addition, may include other pharmaceutical agents such as another anti-viral agents, adjuvants, diluents, buffers, and the like. The compound may thus be administered in dosage formulations containing conventional non-toxic pharmaceutically acceptable carriers, adjuvants and vehicles. The amount of active compound administered will be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions may, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

In embodiments that include a method of inhibiting viral replication or a method of treating a virus infection, the virus may be a DNA virus, which may include, but is not limited to, members of the Herpesviridae, Adenoviridae, Polyomaviridae, Poxyiridae, Papillomaviridae, Anelloviridae or Parvoviridae families of viruses. Examples of particular viruses include, but are not limited to, cowpox, vaccinia, monkeypox, smallpox, other poxviruses including variola virus and drug-resistant strains thereof, Herpes simplex I, Herpes simplex II, cytomegalovirus, Varicella-Zoster Virus, Epstein-Barr Virus, Human Herpes Virus Type 6, Human Herpes Virus Type 8, Papilomavirus, BK virus and Adenovirus. The virus may also be an RNA virus, which may include, but is not limited to, members of the Retroviridae or Hepadnaviridae. Examples of particular viruses include, but are not limited to, HIV and hepatitis A, B or C virus. When inhibiting viral replication or treating a virus infection, an antiviral compound, or a salt thereof, or a combination thereof, may be applied or administered. The virus-infected cell may be in an individual, may be in an isolated organ, or may be in culture. An individual may be a person or an animal.

The present invention may be better understood by referring to the accompanying examples, which are intended for illustration purposes only and should not in any sense be construed as limiting the scope of the invention.

EXAMPLES

Synthesis

According to their antiviral activity spectrum, the ANPs can be classified to two categories: the "HPMP" derivatives, which are active against a broad variety of DNA viruses (examples include ANPs 1 and 2), and the "PME" and "PMP" derivatives (examples include ANPs 3 and 4), which are primarily active against hepadna- and retroviruses [1]. From the structural point of view, the major difference between these two groups of ANPs consists in the presence of a hydroxymethylene function in compounds belonging to the first group, which allows their conversion into the corresponding cyclic derivatives followed by the attachment of an esterifying promoiety (general structure 5, FIG. 1). For the compounds in the second group, formation of only acyclic derivatives 6 is possible (FIG. 1).

Amido tyrosine esters of cyclic (S)-HPMPA and (S)-HPMPC 8a-f have been synthesized as described in Scheme 1 (Scheme 1 shows the synthesis of tyrosine cHPMPA and cHPMPC conjugates 8a-f, with reagents and conditions being: a) PyBOP, DIEA, DMF, 35-40° C., 2 h or overnight, and b) TFA, CH$_2$Cl$_2$, rt). Commercially unavailable NHBoc tyrosine amino acid alkyl amides 7a-e were synthesized in our laboratory according to the literature methods [9]. The coupling reactions between (S)-HPMPA 1 or (S)-HPMPC 2 and amino acid derivatives 7a-e were performed in dimethylformamide (DMF) using diisopropylethylamine (DIEA) as a base and benzotriazol-1-yl-oxytripyrrolidinophosphonium hexafluorophosphate (PyBOP) as a coupling reagent at 35-40° C. The reaction was monitored by $^{31}$P-NMR and stopped when cHPMPA, which is firstly formed in the reaction, was no longer present. After solvent removal under vacuum, the residue was purified using column chromatography yielding BOC-protected intermediates Boc-8a-f as mixtures of two diastereoisomers, major, (A) and minor, (B), in a ratio close to 4:1.

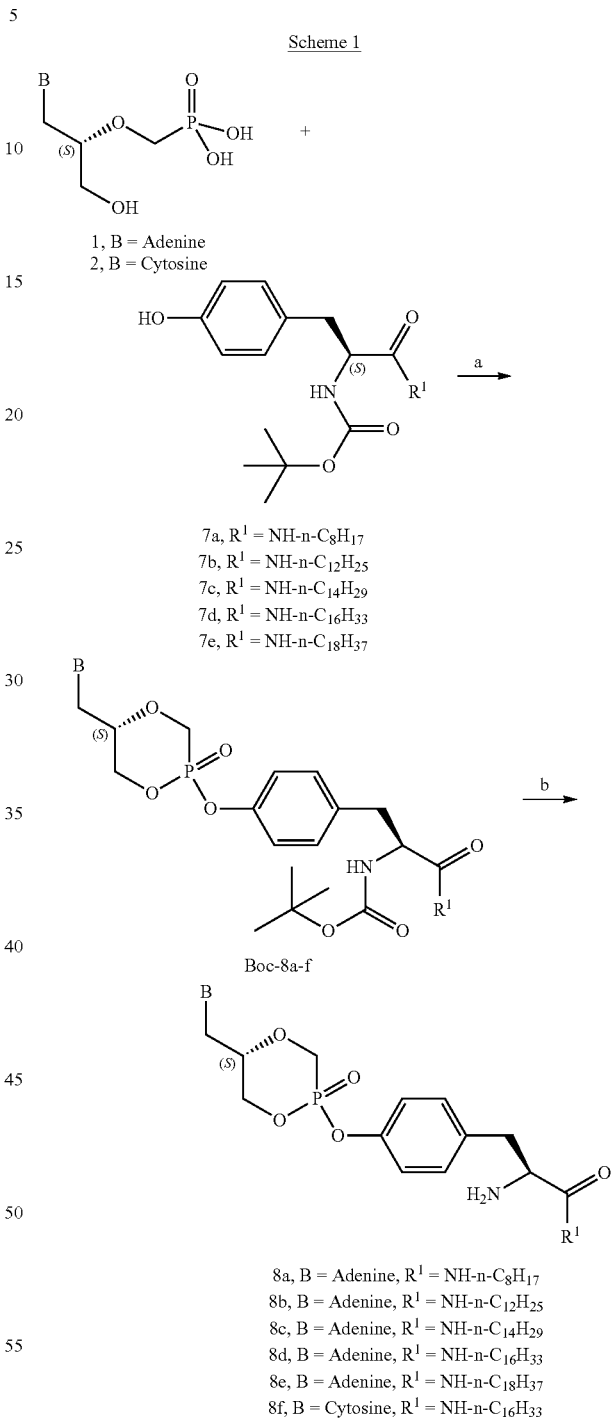

In the next step, the tert-butoxycarbonyl group was removed using trifluoroacetic acid (TFA) in dichloromethane (CH$_2$Cl$_2$). The reaction mixture was purified by column chromatography, eluting the product with a mixture of methanol and dichloromethane with addition of a small amount of TFA (v/v 0.5%) to prevent decomposition of the conjugate during purification. The compounds 8a-f were finally precipitated from methanol by addition of diethyl ether (Et₂O) as mixtures of two diastereomers, major, (A) and minor, (B), in a ratio close to 4:1.

Acyclic amido tyrosine esters of (S)-HPMPA and (S)-HPMPC (9a-f) have been obtained via hydrolysis of the cyclic analogs 8a-f using 14.8 M aq. NH₄OH at 45° C. as depicted in Scheme 2 (Scheme 2 shows the synthesis of tyrosine (S)-HPMPA conjugates 9a-f, with reagents and conditions: a) 14.8 M aq. NH₄OH, 45° C.). To increase solubility of 8b-f acetonitrile (ACN) was added to the reaction mixture. In the case of 9a, the products were separated using HPLC, whereas the acyclic compounds 9b-f were purified by silica gel column chromatography.

Scheme 2

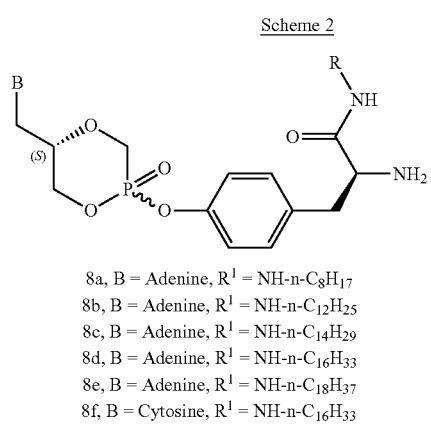

8a, B = Adenine, R¹ = NH-n-C₈H₁₇
8b, B = Adenine, R¹ = NH-n-C₁₂H₂₅
8c, B = Adenine, R¹ = NH-n-C₁₄H₂₉
8d, B = Adenine, R¹ = NH-n-C₁₆H₃₃
8e, B = Adenine, R¹ = NH-n-C₁₈H₃₇
8f, B = Cytosine, R¹ = NH-n-C₁₆H₃₃ a ⟶

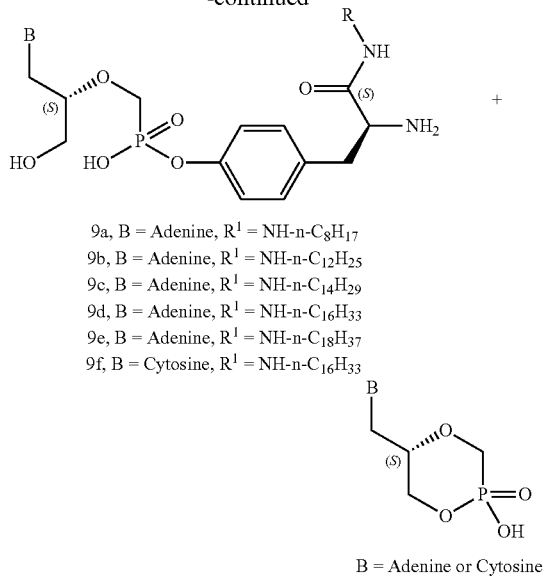

9a, B = Adenine, R¹ = NH-n-C₈H₁₇
9b, B = Adenine, R¹ = NH-n-C₁₂H₂₅
9c, B = Adenine, R¹ = NH-n-C₁₄H₂₉
9d, B = Adenine, R¹ = NH-n-C₁₆H₃₃
9e, B = Adenine, R¹ = NH-n-C₁₈H₃₇
9f, B = Cytosine, R¹ = NH-n-C₁₆H₃₃

B = Adenine or Cytosine

In order to obtain tyrosine conjugates of PMEA and PMP-DAP direct PyBOP-mediated coupling of the promoiety with PMEA was attempted as with the (S)-HPMPA and (S)-HPMPC prodrug synthesis. However, the acyclic HOBt-intermediate of PMEA was significantly more stable under the reaction conditions than the cyclic HOBt-HPMP-based intermediate from (S)-HPMPA or (S)-HPMPC, and did not react with the promoiety.

Scheme 3

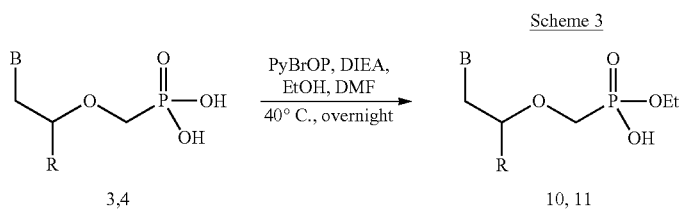

3, 10, 12, 14: R = H, B = adenine
4, 11, 13, 15: R = Me, B = 2,6-diaminopurine (PMP)

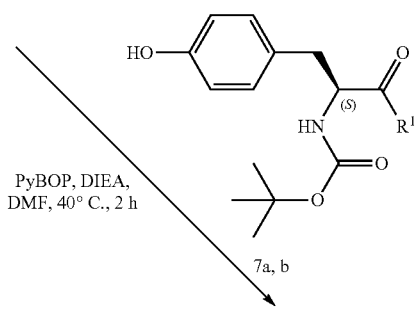

PyBOP, DIEA,
DMF, 40° C., 2 h

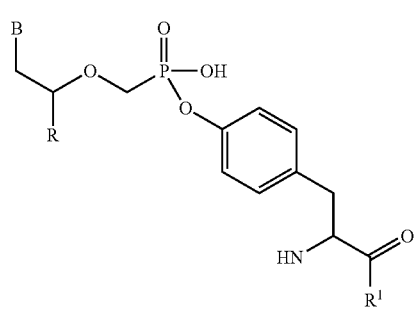

14a: R = H, R¹ = NHC₈H₁₇
14b: R = H, R¹ = NHC₁₆H₃₃
15a: R = Me, R¹ = NHC₈H₁₇

BTMS, CH₃CN, 75° C., 4 h a: R¹ = NHC₈H₁₇,
b: R¹ = NHC₁₆H₃₃

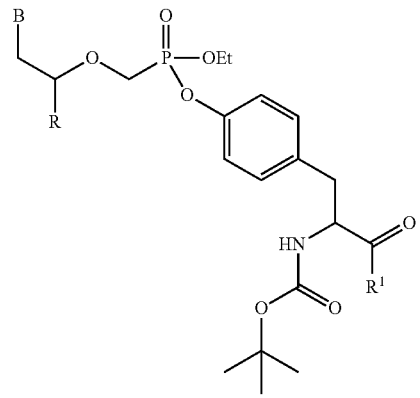

12a, b; 13a

Consequently, we developed an alternative method (Scheme 3, which shows the synthesis of tyrosine conjugates of PMEA (14a, b) and (R)-PMPDAP (15a)). The first step involves masking one negative charge on the phosphonate group by preparation of the ethyl mono-ester (10, 11), which in contrast to the tyrosine derivative is readily formed via PyBrOP-mediated coupling. Conjugation of this derivative to the Boc-protected promoiety is then performed by PyBOP coupling, giving rise to a mixed diester of PMEA or (R)-PMPDAP (12, 13a). Silyldealkylation by BTMS in acetonitrile regioselectively removes the ethyl ester, and methanolysis produces the final compounds 14a, b, 15a in moderate to good overall yields. Conveniently, the amino group is also deprotected in one pot under these conditions.

In Vitro Antiviral Activity

The newly synthesized amido tyrosine ester conjugates, as well as parent compounds (S)-HPMPA, (S)-HPMPC, their cyclic forms cHPMPA and cHPMPC, PMEA and (R)-PMPDAP were evaluated for in vitro antiviral activity against various DNA viruses including, human cytomegalovirus (HCMV), and two poxviruses (vaccinia and cowpox viruses). Results are shown in Table 1.

TABLE 1

Antiviral activity and cytotoxicity of amido tyrosine ester conjugates of (S)-HPMPA, (S)-HPMPC, cHPMPA, PMEA and (R)-PMPDAP.

| Compound | Antiviral activity, IC$_{50}$ (µM) | | | Cytotoxicity IC$_{50}$ (µM) |
|---|---|---|---|---|
| | HCMV | Vaccinia | Cowpox | |
| (S)-HPMPA | 6.0 | 2.5 | 20 | >100 |
| (S)-cHPMPA | 1.5 | 1.0 | 2.5 | >100 |
| (L)-Tyr(NHC₈H₁₇)—(S)-cHPMPA (8a) TFA salt | 0.3 | 1.5 | 3.0 | 100 |
| (L)-Tyr(NHC₁₂H₂₅)—(S)-cHPMPA (8b) TFA salt | <10⁻⁶ | nd$^a$ | nd$^a$ | 15 |
| (L)-Tyr(NHC₁₄H₂₉)—(S)-cHPMPA (8c) TFA salt | <10⁻⁶ | nd$^a$ | nd$^a$ | 15 |
| (L)-Tyr(NHC₁₆H₃₃)—(S)-cHPMPA (8d) TFA salt | <10⁻⁶ | 0.006 | <0.1 | 11 |
| (L)-Tyr(NHC₁₈H₃₇)—(S)-cHPMPA (8e) TFA salt | <10⁻⁶ | nd$^a$ | nd$^a$ | 10 |
| (L)-Tyr(NHC₈H₁₇)—(S)-HPMPA (9a) ammonium salt | <0.1 | nd$^a$ | nd$^a$ | nd$^a$ |
| (L)-Tyr(NHC₁₂H₂₅)—(S)-HPMPA (9b) ammonium salt | <10⁻⁶ | nd$^a$ | nd$^a$ | 15 |
| (L)-Tyr(NHC₁₄H₂₉)—(S)-HPMPA (9c) ammonium salt | <10⁻⁶ | nd$^a$ | nd$^a$ | 20 |
| (L)-Tyr(NHC₁₆H₃₃)—(S)-HPMPA (9d) ammonium salt | <10⁻⁶ | 0.003 | <0.1 | 15 |
| (L)-Tyr(NHC₁₈H₃₇)—(S)-HPMPA (9e) ammonium salt | <10⁻⁶ | nd$^a$ | nd$^a$ | 10 |
| (S)-HPMPC | 0.3 | 10 | 25 | >100 |
| (L)-Tyr(NHC₁₆H₃₃)—(S)-cHPMPC (8f) TFA salt | <10⁻⁶ | nd$^a$ | nd$^a$ | 15 |
| (L)-Tyr(NHC₁₆H₃₃)—(S)-HPMPC (9f) ammonium salt | <10⁻⁶ | nd$^a$ | nd$^a$ | 90 |
| PMEA | 25 | >100 | >100 | >100 |
| (L)-Tyr(NHC₈H₁₇)-PMEA (14a) HBr salt | 35 | 50 | >100 | 100 |
| (L)-Tyr(NHC₁₆H₃₃)-PMEA (14b) HBr salt | 2.5 | 4.0 | 20 | 15 |
| (R)-PMPDAP | >100 | >100 | >100 | >100 |
| (L)-Tyr(NHC₈H₁₇)—(R)-PMPDAP (15a) HBr salt | >100 | >100 | >100 | >100 |
| DHPG Ganciclovir | 3.0 | | | |
| 3L 2-Acetylpyridine thiosemicarbazone | | | | 2 |

$^a$not defined

Antiviral and Cytotoxicity Assays

Propagation of Cells and Virus

The routine growth and passage of KB cells were performed in monolayer cultures using minimal essential medium (MEM) with either Hanks salts [MEM(H)] or Earle salts [MEM(E)] supplemented with 5% fetal bovine serum. Cells were routinely enumerated with a Coulter Counter model ZF equipped with 100 mm orifice. KB cells were plated at 1×10⁵ cells/well using 24-well cluster dishes. The routine growth and passage of primary human foreskin fibroblast (HFF) cells and methods for propagation and titration of virus have been previously described by Turk et al. [10]. Viral pools were prepared in HFF cells and were diluted to provide working stocks. All viruses were titered using monolayer cultures of HFF cells [11]. Following incubation for three days (poxviruses) or 10-12 days (HCMV), the cells were fixed and stained with 0.1% crystal violet in 20% methanol and macroscopic plaques (poxviruses) or microscopic plaques (HCMV) enumerated.

Assays for Antiviral Activity

The effects of compounds on the replication all the viruses were measured using plaque reduction assays [10,12]. Briefly, for poxviruses, the virus used was diluted in MEM containing 10% FBS to a desired concentration which would give 50 plaques per well in 6-well cluster plates. After a 1 h incubation period, an equal amount of 1% agarose was added to an equal volume of each drug dilution (100 μM and ending with 0.03 μM in a methocel overlay). The drug-methocel mixture was added, and the plates were incubated for 3 days, after which cells were stained with 0.1% crystal violet in 20% methanol. Similar techniques were used for HCMV differing in that 100 plaques were used per well in 24-well cluster plates and incubation was approximately 10 days for HCMV. Drug effects were calculated as a percentage of the reduction in plaque number in the presence of each drug concentration compared to the numbers obtained in the absence of drug. Cidofovir ((S)-HPMPC, CDV) and ganciclovir (GCV) were used as positive controls in experiments with poxviruses and HCMV, respectively. 50% inhibitory concentrations ($IC_{50}$) were calculated from the regression lines using the methods described by Goldstein [13]. Samples containing positive controls were used in all assays.

Cytotoxicity Assays.

Effects of all compounds on HFF cells used in plaque reduction assays were scored visually for cytotoxicity. Cytotoxicity to KB cell growth was tested using a colorimetric assay. In HFF cells, cytopathology was estimated at 20- to 60-fold magnification in areas of the assay plate not affected with virus infection and scored on a zero to four plus basis. Cells were scored on the day of staining. In KB cells, the effect of compounds during two population doublings of KB cells was determined by crystal violet staining and spectrophotometric quantization of dye eluted from stained cells as described earlier [11]. Briefly, 96-well cluster dishes were plated with KB cells at 5000 cells per well. After overnight incubation at 37° C., test compound was added in triplicate at eight concentrations. Plates were incubated at 37° C. for 48 h in a $CO_2$ incubator, rinsed, fixed with 95% ethanol, and stained with 0.1% crystal violet. Acidified ethanol was added and plates read at 570 nm in a spectrophotometer designed to read 96-well ELISA assay plates. Dose-response relationships were constructed by linearly regressing the percent inhibition of parameters derived in the preceding sections against log drug concentrations. The 50% inhibitory concentrations were calculated from the regression lines using the methods described by Goldstein [13].

Experimental Section $^1$H and $^{31}$P NMR spectra were obtained on Varian 500-MR and Brucker AMX-500 2-Channel NMR spectrometers. Chemical shifts (δ) are reported in parts per million (ppm) relative to internal $CD_3OD$ (δ3.34 $^1$H NMR) and $CDCl_3$ (δ7.26 $^1$H NMR) or external 85% $H_3PO_4$ (δ0.00 $^{31}$P NMR). $^{31}$P NMR spectra were proton-decoupled, and $^1$H and $^{13}$C coupling constants (J values) are quoted in Hz. The following NMR abbreviations are used: s (singlet), d (doublet), m (unresolved multiplet), dd (doublet of doublet), ddd (doublet of doublet of doublet), br (broad signal). The concentration of the NMR samples was in the range of 2-20 mg/ml. MS was performed on a Finnigan LCQ Deca XP Max mass spectrometer in positive ion mode. The names of the compounds were assigned using ACD labs 12.0. Boc-protected tyrosine amides (7a-e) were synthesized as described below. All other reagents were purchased from commercial sources and used as obtained, unless specified otherwise.

Amidation of Boc-Protected (L)-Tyrosine

Boc-(L)-tyrosine (commercially available) (4.6 mmol, 1.30 g) was suspended in dry $CH_2Cl_2$ (20 mL) and the suspension was cooled to 0° C. before addition of N-hydroxybenzotriazole (HOBt) hydrate (6.0 mmol, 0.81 g) and $Et_3N$ (5.1 mmol, 0.71 mL). The reaction mixture was kept at 0° C. for 15 min before 1-ethyl-3-(3-dimethylaminopropyl)-carbodiimide (EDC) hydrochloride (6.0 mmol, 1.15 g) and the corresponding alkylamine (5.1 mmol) was added sequentially. The reaction mixture was stirred at room temperature overnight. An additional 30 mL of $CH_2Cl_2$ was added, and the organic layer was washed successively with 1.6 M citric acid (25 mL), saturated $NaHCO_3$ (25 mL), and saturated NaCl (20 mL). The organic phase was dried over $Na_2SO_4$ and concentrated under vacuum. The products (7a-e) were used in the next step without further purification.

Synthesis of Tyrosine Cyclic (S)-HPMPA and (S)-HPMPC Conjugates 8a-f

General Procedure for PyBOP Coupling

To a suspension of (S)-HPMPA 1 (1 mmol) in dry DMF (10 mL), dry DIEA (10 mmol, 1.8 mL), BOC-protected amino acid 7a-e and PyBOP (1 mmol) were added. Obtained mixture was stirred under $N_2$ at 40° C. for 2 h or overnight. The reaction was monitored by $^{31}$P NMR, and additional portions of PyBOP were added as necessary. After reaction completion DMF and DIEA were removed under vacuum. The residue was washed with diethyl ether and purified by silica gel column chromatography [eluent: $CH_2Cl_2$:acetone:$CH_3OH$ (60:30:0-10)]. Solvents were removed under vacuum to furnish N-Boc protected compounds Boc-8a-f.

Boc-Deprotection. General Procedure

TFA (2 mL) was added to a solution of the Boc-protected derivatives Boc-8a-f dissolved in dry $CH_2Cl_2$ (8 mL). After stirring overnight at room temperature, volatiles were removed under vacuum. The residue was purified by silica gel column chromatography for compounds 8a-f [eluent: $CH_2Cl_2$:TFA:MeOH (89.5:0.5:0-15)]. After removing the solvent, compounds 8a-f were precipitated with diethyl ether, filtered and dried in vacuum to give TFA salts of final products as white powders. In text below the diastereomers are denoted as A and B.

O-[(5S)-5-[(6-Amino-9H-purin-9-yl)methyl]-2-oxido-1,4,2-dioxaphosphinan-2-yl]-N-octyl-(L)-tyrosinamide (8a)

Overall yield 48%. Obtained as a TFA salt; mixture of diastereomers ($S_p/R_p$, 4.2:1). $^1$H NMR (400 MHz, $CD_3OD$): δ 8.36 (s, 0.8H, 2-H, ($S_p$)), 8.35 (s, 0.2H, 2-H, ($R_p$)), 8.29 (s, 0.8H, 8-H, ($S_p$)), 8.25 (s, 0.2H, 8-H, ($R_p$)), 7.33-7.30 (m, 2H, aromatic), 7.24-7.21 (m, 2H, aromatic), 4.77 (ddd, J=12.1, 12.1, 2.8 Hz, 0.8H, $CH_aH_bO$, ($S_p$)), 4.67 (dd, J=14.9, 8.4 Hz, 0.8H, $CH_aH_bN$, ($S_p$)), 4.59-4.32 (m, 4.4H, $CH_aH_bO$, ($R_p$), $CH_aH_bN$ ($R_p$), $CH_aH_bO$, $CH_aH_bN$, $CH_aH_bP$ and CHO), 4.21 (dd, J=14.8, 4.3 Hz, 0.8H, $CH_aH_bP$, ($S_p$)), 4.12 (dd, J=15.3, 1.3 Hz, 0.2H, $CH_aH_bP$, ($R_p$)), 4.00-3.97 (m, 1H, $CHNH_2$, ($S_p$ and $R_p$)), 3.23-3.05 (m, 4H, $CH_2$(Tyr), $CH_2NHCO$), 1.46-1.41 (m, 2H, $NHCH_2CH_2$), 1.35-1.24 (m, 10H, $5CH_2$), 0.92 (t, J=6.9 Hz, 3H, $CH_3CH_2$). $^{31}$P NMR (162 MHz, $CD_3OD$): δ 11.4 (0.81P ($S_p$)), 9.9 (0.19P, ($R_p$)).

O-[(5S)-5-[(6-Amino-9H-purin-9-yl)methyl]-2-oxido-1,4,2-dioxaphosphinan-2-yl]-N-dodecyl-(L)-tyrosinamide (8b)

Overall yield 60%. Obtained as a TFA salt; mixture of diastereomers ($S_p/R_p$, 3.8:1). $^1$H NMR (400 MHz, $CD_3OD$):

δ 8.37 (s, 1H, 2-H, ($S_p$ and $R_p$)), 8.30 (s, 0.8H, 8-H, ($S_p$)), 8.25 (s, 0.2H, 8-H, ($R_p$)), 7.33-7.30 (m, 2H, aromatic), 7.24-7.21 (m, 2H, aromatic), 4.77 (ddd, J=12.1, 12.1, 2.8 Hz, 0.8H, $CH_aH_bO$, ($S_p$)), 4.67 (dd, J=15.0, 8.4 Hz, 0.8H, $CH_aH_bN$, ($S_p$)), 4.59-4.33 (m, 4.4H, $CH_aH_bO$, ($R_p$), $CH_aH_bN$ ($R_p$), $CH_aH_bO$, $CH_aH_bN$, $CH_aH_bP$ and CHO), 4.21 (dd, J=14.8, 4.3 Hz, 0.8H, $CH_aH_bP$, ($S_p$)), 4.12 (dd, J=15.3, 1.3 Hz, 0.2H, $CH_aH_bP$, ($R_p$)), 4.01-3.97 (m, 1H, $CHNH_2$, ($S_p$ and $R_p$)), 3.25-3.05 (m, 4H, $CH_2$(Tyr), $CH_2NHCO$), 1.46-1.39 (m, 2H, $NHCH_2CH_2$), 1.36-1.26 (m, 18H, $9CH_2$), 0.92 (t, J=6.9 Hz, 3H, $CH_3CH_2$). $^{31}$P NMR (162 MHz, $CD_3OD$): δ 11.4 (0.79P($S_p$)), 9.9 (0.19P, ($R_p$)).

O-[(5S)-5-[(6-Amino-9H-purin-9-yl)methyl]-2-oxido-1,4,2-dioxaphosphinan-2-yl]-N-tetradecyl-(L)-tyrosinamide (8c)

Overall yield 49%. Obtained as a TFA salt; mixture of diastereomers ($S_p/R_p$, 4.1:1). $^1$H NMR (500 MHz, $CD_3OD$): δ 8.35 (s, 0.8H, 2-H, ($S_p$)), 8.34 (s, 0.2H, 2-H, ($R_p$)), 8.28 (s, 0.8H, 8-H, ($S_p$)), 8.23 (s, 0.2H, 8-H, ($R_p$)), 7.33-7.31 (m, 2H, aromatic), 7.24-7.21 (m, 2H, aromatic), 4.77 (ddd, J=12.1, 12.1, 3.0 Hz, 0.8H, $CH_aH_bO$, ($S_p$)), 4.67 (dd, J=14.9, 8.4 Hz, 0.8H, $CH_aH_bN$, ($S_p$)), 4.59-4.33 (m, 4.4H, $CH_aH_bO$, ($R_p$), $CH_aH_bN$($R_p$), $CH_aH_bO$, $CH_aH_bN$, $CH_aH_bP$ and CHO), 4.21 (dd, J=14.8, 4.3 Hz, 0.8H, $CH_aH_bP$, ($S_p$)), 4.12 (dd, J=15.1, 1.3 Hz, 0.2H, $CH_aH_bP$, ($R_p$)), 4.00-3.97 (m, 1H, $CHNH_2$, ($S_p$ and $R_p$)), 3.25-3.05 (m, 4H, $CH_2$(Tyr), $CH_2NHCO$), 1.46-1.40 (m, 2H, $NHCH_2CH_2$), 1.35-1.25 (m, 22H, $11CH_2$), 0.93 (t, J=7.0 Hz, 3H, $CH_3CH_2$). $^{31}$P NMR (202 MHz, $CD_3OD$): δ 11.7 (0.81P ($S_p$)), 10.1 (0.19P, ($R_p$)).

O-[(5S)-5-[(6-Amino-9H-purin-9-yl)methyl]-2-oxido-1,4,2-dioxaphosphinan-2-yl]-N-hexadecyl-(L)-tyrosinamide (8d)

Overall yield 33%. Obtained as a TFA salt; mixture of diastereomers ($S_p/R_p$, 3.8:1). $^1$H NMR (500 MHz, $CD_3OD$): δ 8.35 (s, 1H, 2-H, ($S_p$ and $R_p$)), 8.28 (s, 0.8H, 8-H, ($S_p$)), 8.23 (s, 0.2H, 8-H, ($R_p$)), 7.33-7.31 (m, 2H, aromatic), 7.24-7.21 (m, 2H, aromatic), 4.77 (ddd, J=12.0, 12.0, 2.8 Hz, 0.8H, $CH_aH_bO$, ($S_p$)), 4.66 (dd, J=15.0, 8.4 Hz, 0.8H, $CH_aH_bN$, ($S_p$)), 4.59-4.33 (m, 4.4H, $CH_aH_bO$, ($R_p$), $CH_aH_bN$ ($R_p$), $CH_aH_bO$, $CH_aH_bN$, $CH_aH_bP$ and CHO), 4.21 (dd, J=14.8, 4.3 Hz, 0.8H, $CH_aH_bP$, ($S_p$)), 4.12 (dd, J=15.2, 1.4 Hz, 0.2H, $CH_aH_bP$ ($R_p$)), 4.02-3.97 (m, 1H, $CHNH_2$, ($S_p$ and $R_p$)), 3.23-3.06 (m, 4H, $CH_2$(Tyr), $CH_2NHCO$), 1.44-1.40 (m, 2H, $NHCH_2CH_2$), 1.35-1.27 (m, 26H, $13CH_2$), 0.93 (t, J=6.9 Hz, 3H, $CH_3CH_2$). $^{31}$P NMR (202 MHz, $CD_3OD$): δ 11.7 (0.80P($S_p$)), 10.1 (0.20P, ($R_p$)).

O-[(5S)-5-[(6-Amino-9H-purin-9-yl)methyl]-2-oxido-1,4,2-dioxaphosphinan-2-yl]-N-octadecyl-(L)-tyrosinamide (8e)

Overall yield 53%. Obtained as a TFA salt; mixture of diastereomers ($S_p/R_p$, 3.8:1). $^1$H NMR (500 MHz, $CD_3OD$): δ 8.36 (s, 1H, 2-H), 8.28 (s, 0.8H, 8-H ($S_p$)), 8.24 (s, 0.2H, 8-H($R_p$)), 7.33-7.31 (m, 2H, aromatic), 7.24-7.21 (m, 2H, aromatic), 4.77 (ddd, J=12.0, 12.0, 2.8 Hz, 0.8H, $CH_aH_bO$ ($S_p$)), 4.67 (dd, J=15.0, 8.5 Hz, 0.8H, $CH_aH_bN$ ($S_p$)), 4.59-4.33 (m, 4.4H, $CH_aH_bO$ ($R_p$), $CH_aH_bN$ ($R_p$), $CH_aH_bO$, $CH_aH_bN$, $CH_aH_bP$ and CHO), 4.21 (dd, J=14.8, 4.3 Hz, 0.8H, $CH_aH_bP$ ($S_p$)), 4.12 (dd, J=15.4, 1.2 Hz, 0.2H, $CH_aH_bP$ ($R_p$)), 4.02-3.98 (m, 1H, $CHNH_2$, ($S_p$ and $R_p$)), 3.25-3.06 (m, 4H, $CH_2$(Tyr), $CH_2NHCO$), 1.46-1.40 (m, 2H, $NHCH_2CH_2$), 1.35-1.25 (m, 30H, $15CH_2$), 0.93 (t, J=6.9 Hz, 3H, $CH_3CH_2$). $^{31}$P NMR (202 MHz, $CD_3OD$): δ 11.7 (0.77P ($S_p$)), 10.1 (0.23P, ($R_p$)).

O-[(5S)-5-[(4-amino-2-oxopyrimidin-1(2H)-yl)methyl]-2-oxido-1,4,2-dioxaphosphinan-2-yl]-N-hexadecyl-(L)-tyrosinamide (8f)

Overall yield 36%. Obtained as a TFA salt; mixture of diastereomers ($S_p/R_p$, 3.0:1). $^1$H NMR (400 MHz, $CD_3OD$): δ 7.77 (d, J=7.5 Hz, 0.75H, 6-H, ($S_p$)), 7.73 (d, J=7.5 Hz, 0.25H, 6-H, ($R_p$)), 7.34-7.22 (m, 4H, aromatic), 6.01-5.98 (m, 1H, 5-H), 4.69-4.62 (m, 0.75H, $CH_aH_bO$, ($S_p$)), 4.55-4.36 (m, 2.25H, $CH_aH_bO$($R_p$), $CH_aH_bO$, $CH_aH_bP$), 4.27-4.23 (m, 1.75H, $CH_aH_bP$ ($S_p$), CHO), 4.17-3.98 (m, 3H, $CH_aH_bP$ ($R_p$), $CH_aH_bN$, $CH_aH_bN$ ($S_p$), $CHNH_2$), 3.83 (dd, J=14.4, 7.5 Hz, 0.25H, $CH_aH_bN$($R_p$)), 3.26-3.05 (m, 4H, $CH_2$(Tyr), $CH_2NHCO$), 1.46-1.43 (m, 2H, $NHCH_2CH_2$), 1.35-1.27 (m, 26H, $13CH_2$), 0.93 (t, J=6.9 Hz, 3H, $CH_3CH_2$). $^{31}$P NMR (162 MHz, $CD_3OD$): δ 11.5 (0.75P ($S_p$)), 10.0 (0.25P, ($R_p$)).

Synthesis of Acyclic Tyrosine (S)-HPMPA and (S)-HPMPC Conjugates 9a-f

General procedure: TFA salt of tyrosine cyclic HPMPA prodrug (8a-f) was mixed with 8 mL of $NH_4OH$ (14.8 M). To increase solubility of 8b acetonitrile was added to the reaction mixture. The mixture was heated at 45° C. until reaction was completed (reaction was monitored by $^{31}$P NMR). In case of 8a, the products were separated using HPLC (isocratic; buffer: $NH_4OAc$, pH 5.5, 30% ACN). Solvents were removed under vacuum and the samples were lyophilized. In case of 8b-f, the products were purified by subsequent washing with $H_2O$ and MeOH. (cHPMPA is soluble in both $H_2O$ and MeOH, whereas the acyclic prodrug is soluble in MeOH only). Finally, acyclic compound 9b-f were purified from the corresponding amino acid N-alkyl amide using silica gel column chromatography [eluent $CH_2Cl_2$: $CH_3OH$:$Et_3N$].

O-[([[(2S)-1-(6-Amino-9H-purin-9-yl)-3-hydroxypropan-2-yl]oxy]methyl)(hydroxy)-phosphoryl]-N-octyl-(L)-tyrosinamide (9a)

Overall yield 44%. Obtained as ammonium acetate salt. $^1$H NMR (500 MHz, $CD_3OD$): δ 8.20 (s, 1H, 2-H), 8.18 (s, 1H, 8-H), 7.14-7.13 (m, 2H, aromatic), 7.06-7.04 (m, 2H, aromatic), 4.48 (dd, J=14.5, 3.7 Hz, 1H, $CH_aH_bN$), 4.41 (dd, J=14.5, 7.0 Hz, 1H, $CH_aH_bN$), 3.92-3.68 (m, 5H, $CHNH_2$, $CH_aH_bO$, $CH_aH_bP$, $CH_aH_bP$, CHO), 3.56 (dd, J=12.3, 4.5 Hz, 1H, $CH_aH_bO$), 3.23-3.18 (m, 2H, $CH_2NHCO$), 3.13 (dd, J=13.6, 5.5 Hz, 1H, $CH_aH_b$(Tyr)), 2.94 (dd, J=13.6, 8.1 Hz, 1H, $CH_aH_b$(Tyr)), 1.51-1.48 (m, 2H, $NHCH_2CH_2$), 1.35-1.32 (m, 100H, $5CH_2$), 0.92 (t, J=6.9 Hz, 3H, $CH_3CH_2$). $^{13}$C NMR (126 MHz, $CD_3OD$): δ 171.6 (CO), 158.0 ($C^6$, adenine), 154.5 ($C^2$, adenine), 154.3 (d, $^2J_{CP}$=7.5 Hz, COP, aromatic), 151.8 ($C^4$, adenine), 144.8 ($C^8$, adenine), 132.1 (2CH, aromatic), 131.4 (ipso-C, aromatic), 123.3 (d, $^3J_{CP}$=3.8 Hz, 2CH, aromatic), 120.6 ($C^5$, adenine), 82.7 (d, $^3J_{CP}$=11.8 Hz, CHO), 67.4 (d, $^1J_{CP}$=162.6 Hz, $CH_2P$), 62.5 ($CH_2OH$), 57.2 ($CHNH_2$), 46.3 ($CH_2N$), 41.5 ($CH_2NH$), 39.7 ($CH_2C_6H_4$), 33.9 ($CH_2$), 31.2 (2$CH_2$), 31.1 ($CH_2$), 28.9 ($CH_2$), 24.6 ($CH_2$), 15.3 ($CH_3$). $^{31}$P NMR (202 MHz, $CD_3OD$): δ 14.8 (s).

O-[([[(2S)-1-(6-Amino-9H-purin-9-yl)-3-hydroxypropan-2-yl]oxy]methyl)(hydroxy)-phosphoryl]-N-dodecyl-(L)-tyrosinamide (9b)

Overall yield 25%. $^1$H NMR (500 MHz, CD$_3$OD): δ 8.20 (s, 1H, 2-H), 8.19 (s, 1H, 8-H), 7.15-7.13 (m, 2H, aromatic), 7.06-7.04 (m, 2H, aromatic), 4.48 (dd, J=14.5, 3.7 Hz, 1H, CH$_a$H$_b$N), 4.41 (dd, J=14.6, 7.0 Hz, 1H, CH$_a$H$_b$N), 3.99 (dd, J=8.3, 6.3 Hz, 1H, CHNH$_2$), 3.90-3.86 (m, 1H, CHO), 3.82 (dd, J=13.0, 9.3 Hz, 1H, CH$_a$H$_b$P), 3.76-3.69 (m, 2H, CH$_a$H$_b$O, CH$_a$H$_b$P), 3.56 (dd, J=12.4, 4.5 Hz, 1H, CH$_a$H$_b$O), 3.27-3.19 (m, 2H, CH$_2$NHCO), 3.15 (dd, J=14.1, 6.1 Hz, 1H, CH$_a$H$_b$(Tyr)), 2.95 (dd, J=14.1, 8.5 Hz, 1H, CH$_a$H$_b$(Tyr)), 1.52-1.49 (m, 2H, NHCH$_2$CH$_2$), 1.35-1.30 (m, 18H, 9CH$_2$), 0.92 (t, J=6.9 Hz, 3H, CH$_3$CH$_2$). $^{13}$C NMR (126 MHz, CD$_3$OD): δ 170.6 (CO), 158.0 (C$^6$, adenine), 154.5 (C$^2$, adenine), 154.4 (d, $^2J_{CP}$=7.6 Hz, COP, aromatic), 151.8 (C$^4$, adenine), 144.8 (C$^8$, adenine), 132.1 (2CH, aromatic), 131.4 (ipso-C, aromatic), 123.5 (d, $^3J_{CP}$=3.9 Hz, 2CH, aromatic), 120.5 (C$^5$, adenine), 82.7 (d, $^3J_{CP}$=11.8 Hz, CHO), 67.5 (d, $^1J_{CP}$=162.7 Hz; CH$_2$P), 62.5 (CH$_2$OH), 56.9 (CHNH$_2$), 46.3 (CH$_2$N), 41.5 (CH$_2$NH), 39.1 (CH$_2$C$_6$H$_4$), 33.9 (CH$_2$), 31.64 (CH$_2$), 31.62 (CH$_2$), 31.60 (CH$_2$), 31.5 (CH$_2$), 31.3 (CH$_2$), 31.2 (CH$_2$), 31.1 (CH$_2$), 28.9 (CH$_2$), 24.6 (CH$_2$), 15.3 (CH$_3$). $^{31}$P NMR (202 MHz, CD$_3$OD): δ 14.9 (s).

O-[([[(2S)-1-(6-Amino-9H-purin-9-yl)-3-hydroxypropan-2-yl]oxy]methyl)(hydroxy)-phosphoryl]-N-tetradecyl-(L)-tyrosinamide (9c)

Overall yield 38%. $^1$H NMR (500 MHz, CD$_3$OD): δ 8.20 (s, 1H, 2-H), 8.19 (s, 1H, 8-H), 7.15-7.13 (m, 2H, aromatic), 7.06-7.05 (m, 2H, aromatic), 4.48 (dd, J=14.6, 3.8 Hz, 1H, CH$_a$H$_b$N), 4.42 (dd, J=14.6, 7.0 Hz, 1H, CH$_a$H$_b$N), 3.99 (dd, J=8.5, 6.2 Hz, 1H, CHNH$_2$), 3.90-3.86 (m, 1H, CHO), 3.82 (dd, J=13.1, 9.3 Hz, 1H, CH$_a$H$_b$P), 3.76-3.69 (m, 2H, CH$_a$H$_b$O, CH$_a$H$_b$P), 3.56 (dd, J=12.4, 4.6 Hz, 1H, CH$_a$H$_b$O), 3.26-3.19 (m, 2H, CH$_2$NHCO), 3.16 (dd, J=14.0, 6.0 Hz, 1H, CH$_a$H$_b$(Tyr)), 2.95 (dd, J=14.1, 8.6 Hz, 1H, CH$_a$H$_b$(Tyr)), 1.52-1.49 (m, 2H, NHCH$_2$CH$_2$), 1.36-1.30 (m, 22H, 11CH$_2$), 0.92 (t, J=7.0 Hz, 3H, CH$_3$CH$_2$). $^{13}$C NMR (126 MHz, CD$_3$OD): δ 170.5 (CO), 158.0 (C$^6$, adenine), 154.5 (C$^2$, adenine), 154.4 (d, $^2J_{CP}$=7.6 Hz, COP, aromatic), 151.8 (C$^4$, adenine), 144.8 (C$^8$, adenine), 132.1 (2CH, aromatic), 131.4 (ipso-C, aromatic), 123.5 (d, $^3J_{CP}$=3.9 Hz, 2CH, aromatic), 120.5 (C$^5$, adenine), 82.7 (d, $^3J_{CP}$=11.8 Hz, CHO), 67.5 (d, $^1J_{CP}$=162.6 Hz, CH$_2$P), 62.5 (CH$_2$OH), 56.9 (CHNH$_2$), 46.3 (CH$_2$N), 41.5 (CH$_2$NH), 39.0 (CH$_2$C$_6$H$_4$), 33.9 (CH$_2$), 31.66 (2CH$_2$), 31.64 (CH$_2$), 31.62 (CH$_2$), 31.60 (CH$_2$), 31.54 (CH$_2$), 31.33 (CH$_2$), 31.26 (CH$_2$), 31.1 (CH$_2$), 28.9 (CH$_2$), 24.6 (CH$_2$), 15.3 (CH$_3$). $^{31}$P NMR (202 MHz, CD$_3$OD): δ 14.9 (s).

O-[([[(2S)-1-(6-Amino-9H-purin-9-yl)-3-hydroxypropan-2-yl]oxy]methyl)(hydroxy)-phosphoryl]-N-hexadecyl-(L)-tyrosinamide (9d)

Overall yield 46%. $^1$H NMR (500 MHz, CD$_3$OD): δ 8.21 (s, 1H, 2-H), 8.19 (s, 1H, 8-H), 7.15-7.13 (m, 2H, aromatic), 7.07-7.05 (m, 2H, aromatic), 4.48 (dd, J=14.6, 3.8 Hz, 1H, CH$_a$H$_b$N), 4.41 (dd, J=14.6, 7.0 Hz, 1H, CH$_a$H$_b$N), 3.92 (dd, J=8.6, 6.0 Hz, 1H, CHNH$_2$), 3.89-3.85 (m, 1H, CHO), 3.81 (dd, J=13.1, 9.3 Hz, 1H, CH$_a$H$_b$P), 3.76-3.69 (m, 2H, CH$_a$H$_b$O, CH$_a$H$_b$P), 3.55 (dd, J=12.4, 4.6 Hz, 1H, CH$_a$H$_b$O), 3.26-3.19 (m, 2H, CH$_2$NHCO), 3.15 (dd, J=14.1, 6.0 Hz, 1H, CH$_a$H$_b$(Tyr)), 2.93 (dd, J=14.0, 8.5 Hz, 1H, CH$_a$H$_b$(Tyr)), 1.52-1.49 (m, 2H, NHCH$_2$CH$_2$), 1.36-1.31 (m, 26H, 13CH$_2$), 0.93 (t, J=7.0 Hz, 3H, CH$_3$CH$_2$). $^{13}$C NMR (126 MHz, CD$_3$OD): δ 171.3 (CO), 158.0 (C$^6$, adenine), 154.5 (C$^2$, adenine), 154.3 (d, $^2J_{CP}$=7.7 Hz, COP, aromatic), 151.8 (C$^4$, adenine), 144.8 (C$^8$, adenine), 132.0 (2CH, aromatic), 131.7 (ipso-C, aromatic), 123.4 (d, $^3J_{CP}$=3.9 Hz, 2CH, aromatic), 120.5 (C$^5$, adenine), 82.7 (d, $^3J_{CP}$=11.8 Hz, CHO), 67.4 (d, $^1J_{CP}$=162.7 Hz, CH$_2$P), 62.5 (CH$_2$OH), 57.2 (CHNH$_2$), 46.3 (CH$_2$N), 41.5 (CH$_2$NH), 39.5 (CH$_2$C$_6$H$_4$), 33.9 (CH$_2$), 31.65 (4-CH$_2$), 31.63 (CH$_2$), 31.62 (CH$_2$), 31.60 (CH$_2$), 31.5 (CH$_2$), 31.33 (CH$_2$), 31.26 (CH$_2$), 31.15 (CH$_2$), 28.9 (CH$_2$), 24.6 (CH$_2$), 15.3 (CH$_3$). $^{31}$P NMR (202 MHz, CD$_3$OD): δ 14.9 (s).

O-[([[(2S)-1-(6-Amino-9H-purin-9-yl)-3-hydroxypropan-2-yl]oxy]methyl)-(hydroxy)-phosphoryl]-N-octadecyl-(L)-tyrosinamide (9e)

Overall yield 47%. $^1$H NMR (500 MHz, CD$_3$OD): δ 8.20 (s, 1H, 2-H), 8.19 (s, 1H, 8-H), 7.15-7.13 (m, 2H, aromatic), 7.06-7.05 (m, 2H, aromatic), 4.48 (dd, J=14.6, 3.8 Hz, 1H, CH$_a$H$_b$N), 4.42 (dd, J=14.6, 7.0 Hz, 1H, CH$_a$H$_b$N), 3.99 (dd, J=8.5, 6.2 Hz, 1H, CHNH$_2$), 3.90-3.86 (m, 1H, CHO), 3.82 (dd, J=13.1, 9.3 Hz, 1H, CH$_a$H$_b$P), 3.76-3.69 (m, 2H, CH$_a$H$_b$O, CH$_a$H$_b$P), 3.56 (dd, J=12.4, 4.6 Hz, 1H, CH$_a$H$_b$O), 3.27-3.19 (m, 2H, CH$_2$NHCO), 3.16 (dd, J=14.1, 6.0 Hz, 1H, CH$_a$H$_b$(Tyr)), 2.95 (dd, J=14.1, 8.6 Hz, 1H, CH$_a$H$_b$(Tyr)), 1.52-1.49 (m, 2H, NHCH$_2$CH$_2$), 1.36-1.30 (m, 30H, 15CH$_2$), 0.93 (t, J=6.9 Hz, 3H, CH$_3$CH$_2$). $^{13}$C NMR (126 MHz, CD$_3$OD): δ 170.5 (CO), 158.0 (C$^6$, adenine), 154.5 (C$^2$, adenine), 154.4 (d, $^2J_{CP}$=7.7 Hz, COP, aromatic), 151.8 (C$^4$, adenine), 144.8 (C$^8$, adenine), 132.1 (2CH, aromatic), 131.4 (ipso-C, aromatic), 123.5 (d, $^3J_{CP}$=3.9 Hz, 2CH, aromatic), 120.5 (C$^5$, adenine), 82.7 (d, $^3J_{CP}$=11.8 Hz, CHO), 67.5 (d, $^1J_{CP}$=162.6 Hz, CH$_2$P), 62.5 (CH$_2$OH), 56.9 (CHNH$_2$), 46.3 (CH$_2$N), 41.6 (CH$_2$NH), 39.1 (CH$_2$C$_6$H$_4$), 33.9 (CH$_2$), 31.65 (7CH$_2$), 31.62 (CH$_2$), 31.61 (CH$_2$), 31.55 (CH$_2$), 31.34 (CH$_2$), 31.26 (CH$_2$), 31.15 (CH$_2$), 28.9 (CH$_2$), 24.6 (CH$_2$), 15.3 (CH$_3$). $^{31}$P NMR (202 MHz, CD$_3$OD): δ 14.9 (s).

O-[([[(2S)-1-(4-amino-2-oxopyrimidin-(2H)-yl)-3-hydroxypropan-2-yl]oxy]methyl)-(hydroxy)phosphoryl]-N-hexadecyl-(L)-tyrosinamide (9O)

Overall yield 45%. $^1$H NMR (500 MHz, CD$_3$OD): δ 7.63 (s, 1H, 6-H), 7.19-7.17 (m, 2H, aromatic), 7.13-7.11 (m, 2H, aromatic), 5.82 (s, 1H, 5-H), 4.06 (dd, J=13.9, 3.4 Hz, 1H, CH$_a$H$_b$N), 3.90-3.87 (m, 1H, CHNH$_2$), 3.85-3.80 (m, 2H, CH$_a$H$_b$N, CH$_a$H$_b$P), 3.76-3.68 (m, 3H, CH$_a$H$_b$O, CH$_a$H$_b$P, CHO), 3.53 (dd, J=12.0, 3.8 Hz, 1H, CH$_a$H$_b$O), 3.21 (t, 2H, CH$_2$CH$_2$NH), 3.13 (dd, J=13.9, 6.0 Hz, 1H, CH$_a$H$_b$(Tyr)), 2.91 (dd, J=14.0, 8.5 Hz, 1H, CH$_a$H$_b$(Tyr)), 1.53-1.50 (m, 2H, CH$_2$CH$_2$NH), 1.34-1.32 (m, 26H, 13CH$_2$), 0.93 (t, J=6.9 Hz, 3H, CH$_3$CH$_2$). $^{13}$C NMR (126 MHz, CD$_3$OD): δ 172.0 (CONH), 168.8 (NCON), 160.2 (CNH$_2$), 154.3 (d, $^2J_{CP}$=7.3 Hz, COP, aromatic), 149.8 (C$^6$, cytosine), 132.2 (2CH, aromatic), 131.4 (ipso-C, aromatic), 123.3 (d, $^3J_{CP}$=4.0 Hz, 2CH, aromatic), 96.5 (C$^5$, cytosine), 82.3 (d, $^3J_{CP}$=12.2 Hz, CHO), 67.2 (d, $^1J_{CP}$=161.6 Hz, CH$_2$P), 62.5 (CH$_2$OH), 57.3 (CHNH$_2$), 52.4 (CH$_2$N), 41.5 (CH$_2$NH), 39.9 (CH$_2$C$_6$H$_4$), 33.9 (CH$_2$), 31.66 (5CH$_2$), 31.62 (CH$_2$), 31.61 (CH$_2$), 31.56 (CH$_2$), 31.34 (CH$_2$), 31.28 (CH$_2$), 31.18 (CH$_2$), 28.9 (CH$_2$), 24.6 (CH$_2$), 15.3 (CH$_3$). $^{31}$P NMR (202 MHz, CD$_3$OD): δ 14.7 (s).

cHPMPA $^1$H NMR (400 MHz, D$_2$O): δ 8.17 (s, 1H, 8-H), 8.14 (s, 1H, 2-H), 4.28-4.01 (m, 5H), 3.79 (dd, $^2$J$_{HP}$=8.4 Hz, J$_{gem}$=14.1 Hz), 3.54 (dd, $^2$J$_{HP}$=2.3 Hz, J$_{gem}$=14.1 Hz). $^{31}$P NMR (202 MHz, D$_2$O): δ 9.23 (s).

Synthesis of Tyrosine Conjugates of PMEA and (R)-PMPDAP 14a,b, 15a

Synthesis of Mono-Ethyl Esters of PMEA (10) and (R)-PMPDAP (11)

General Procedure

To a suspension of PMEA or (R)-PMPDAP (0.2 mmol) in dry DMF (5 mL), dry DIEA (2.0 mmol) was added. The reaction flask was warmed by a heat gun to facilitate the dissolution of the PMEA/PMPDAP salt. The volatiles were then removed under vacuum. The procedure was repeated twice. To the residue, anhydrous DMF (1.5 mL), anhydrous DIEA (2.0 mmol), anhydrous EtOH (8.0 mmol), and PyBrOP (0.3 mmol) were added consequently. The reaction mixture was stirred under N$_2$ at 40° C. overnight. The reaction was monitored by $^{31}$P NMR for the appearance of a peak at 10-11 ppm. After reaction was complete, DMF, DIEA and EtOH were removed under vacuum. The residue was co-evaporated twice with DMF to remove EtOH traces and dried under vacuum to give mono-ethyl ester of PMEA or PMPDAP in yield 60-76% used for the next step without further purification.

Synthesis of Mixed Diesters of PMEA (12a,b) or PMPDAP (13a)

General Procedure.

To a suspension of mono-ethyl ester of PMEA (10) or PMPDAP (11) (0.15 mmol) in anhydrous DMF (2 mL), anhydrous DIEA (1.5 mmol), relevant Boc-protected amino acid (0.6 mmol) was added following by the addition of PyBOP (0.3 mmol). The reaction mixture was stirred under N$_2$ at 40° C. for 2 h. The reaction was monitored by $^{31}$P NMR, and additional portions of PyBOP were added as necessary. After reaction was complete, DMF and DIEA were removed under vacuum. The residue was extracted with diethyl ether and purified by silica gel column chromatography [CH$_2$Cl$_2$, CH$_2$Cl$_2$:CH$_3$OH (gradient)]. Solvents were removed under vacuum to furnish Boc-protected mixed diester of PMEA (12a, b) or PMPDAP (13) in 67-85% yield.

O-[{[2-(6-Amino-9H-purin-9-yl)ethoxy]methyl}(ethoxy)phosphoryl]-N-octyl-L-tyrosinamide (12a)

$^1$H NMR (500 MHz, CD$_3$OD): δ 8.21 and 8.11 (s, 2H, H—C$^2$ and H—C$^8$, adenine), 7.19 (d, J=7.8 Hz, 2H, aromatic), 6.97 (d, J=8.3 Hz, 2H, aromatic), 4.46 (t, J=4.9 Hz, 2H, CH$_2$N), 4.24 (m, 1H, CHNH$_2$ (Tyr)), 4.13 (m, 2H, OCH$_2$CH$_3$), 4.03 (2dd, 2H, CH$_2$P), 3.99 (t, J=4.7 Hz, 2H, CH$_2$O), 3.15 (m, 2H, CH$_2$N(C$_8$H$_{17}$)), 3.03 (dd, J=13.7, 6.4 Hz, 1H, CH$_a$H$_b$ (Tyr)), 2.83 (dd, J=13.7, 8.8 Hz, 1H, CH$_a$H$_b$(Tyr)), 1.39 (s, 9H, (CH$_3$)$_3$), 1.29 (m, 12H, (CH$_2$)$_6$), 1.25 (t, J=7.3 Hz, OCH$_2$CH$_3$), 0.91 (t, J=6.9 Hz, 3H, CH$_3$). $^{31}$P NMR (202 MHz, CD$_3$OD): δ 18.29

O-[{[2-(6-amino-9H-purin-9-yl)ethoxy]methyl}(ethoxy)phosphoryl]-N-hexadecyl-L-tyrosinamide (12b)

$^1$H NMR (500 MHz, CD$_3$OD): δ 8.23 and 8.12 (s, 2H, H—C$^2$ and H—C$^8$, adenine), 7.20 (d, J=7.8 Hz, 2H, aromatic), 6.98 (d, J=7.9 Hz, 2H, aromatic), 4.47 (t, J=4.9 Hz, 2H, CH$_2$), 4.25 (m, 1H, CHNH$_2$ (Tyr)), 4.15 (m, 2H, OCH$_2$CH$_3$), 4.05 (m, 2H, CH$_2$P), 4.00 (m, 2H, CH$_2$), 3.17 (m, 2H, CH$_2$N(C$_{16}$H$_{33}$)), 3.04 (dd, J=13.7, 5.8 Hz, 1H, CH$_a$H$_b$ (Tyr)), 2.84 (dd, J=13.7, 8.8 Hz, 1H, CH$_a$H$_b$(Tyr)), 1.5-1.24 (m, 40H, (CH$_3$)$_3$, (CH$_2$)$_{14}$), OCH$_2$CH$_3$), 0.93 (t, J=6.9 Hz, 3H, CH$_3$). $^{31}$P NMR (202 MHz, CD$_3$OD): δ 20.42

O-[({[(2R)-1-(2,6-Diamino-9H-purin-9-yl)propan-2-yl]oxy}methyl)(ethoxy)phosphoryl]-N-octyl-L-tyrosinamide (13a)

$^1$H NMR (500 MHz, CD$_3$OD): δ 7.75, 7.73 (2s, 1H, H—C$^8$, DAP), 7.21, 7.16, 7.0, 6.92 (4d, J=8.3 Hz, 4H, aromatic), 4.25-3.95 (m, 7H, CH$_2$N, CHNH$_2$ (Tyr), OCH$_2$CH$_3$, CHO, CH$_a$H$_b$P), 3.86 (2d, 1H, CH$_a$H$_b$P), 3.13 (m, 2H, CH$_2$N(C$_8$H$_{17}$)), 3.01 (m, 1H, CH$_a$H$_b$ (Tyr)), 2.81 (dd, J=13.7, 8.4 Hz, 1H, CH$_a$H$_b$(Tyr)), 1.45-1.19 (m, (CH$_3$)$_3$, (CH$_2$)$_6$), OCH$_2$CH$_3$), 0.88 (t, J=6.9 Hz, 3H, CH$_3$). $^{31}$P NMR (202 MHz, CD$_3$OD): δ 20.0, 19.3

BTMS-Mediated Tandem De-Ethylation and Boc-Deprotection.

General Procedure.

Boc-protected mixed diester of PMEA or PMPDAP (0.1 mmol) was dissolved in 3 ml of anhydrous CH$_3$CN following by addition of BTMS (1.0 mmol). The mixture was refluxed during 4 h. BTMS was removed under vacuum and mixture was co-evaporated with CH$_3$CN twice before the residue was re-dissolved in MeOH. MeOH was then removed under vacuum and the residue was purified by precipitation using EtOH and Et$_2$O to provide final compounds as HBr salts in 25-53% overall yields.

O-[{[2-(6-Amino-9H-purin-9-yl)ethoxy]methyl}(hydroxy)phosphoryl]-N-octyl-L-tyrosinamide (14a)

$^1$H NMR (500 MHz, CD$_3$OD): δ 8.42 (s, 2H, H—C$^2$ and H—C, adenine), 7.26 (d, J=8.3 Hz, 2H, aromatic), 7.15 (d, J=7.8 Hz, 2H, aromatic), 4.58 (t, J=4.9 Hz, 2H, CH$_2$), 4.05 (t, J=5.1 Hz, 2H, CH$_2$), 4.01 (t, J=7.3 Hz, 1H, CHNH$_2$ (Tyr)), 3.93 (d, J=8.3 Hz, 2H, CH$_2$P), 3.25-3.14 (m, 3H, CH$_a$H$_b$ (Tyr) and CH$_2$N(C$_8$H$_{17}$)), 3.06 (dd, J=14.2, 7.8 Hz, 1H, CH$_a$H$_b$ (Tyr)), 1.47 (m, J=6.9 Hz, 2H, CH$_2$CH$_2$N (C$_8$H$_7$)), 1.32 (m, 10H, (CH$_2$)$_5$), 0.93 (t, J=6.9 Hz, 3H, CH$_3$). $^{31}$P NMR (202 MHz, CD$_3$OD): δ 14.45. ESI-MS: m/z calcd 547.27 (M+H)$^+$. found 548.5 (M+H)$^+$.

O-[{[2-(6-Amino-9H-purin-9-yl)ethoxy]methyl}(hydroxy)phosphoryl]-N-hexadecyl-L-tyrosinamide (14b)

$^1$H NMR (500 MHz, CD$_3$OD): δ 8.42 (s, 2H, H—C$^2$ and H—C$^8$, adenine), 7.26 (d, J=8.8 Hz, 2H, aromatic), 7.15 (d, J=8.3 Hz, 2H, aromatic), 4.58 (t, J=4.9 Hz, 2H, CH$_2$), 4.05 (t, J=4.9 Hz, 2H, CH$_2$), 4.01 (t, J=7.3 Hz, 1H, CHNH$_2$ (Tyr)), 3.93 (d, J=8.4 Hz, 2H, CH$_2$P), 3.25-3.16 (m, 3H, CH$_a$H$_b$ (Tyr) and CH$_2$N(C$_{16}$H$_{33}$)), 3.05 (dd, J=14.2, 7.9 Hz, 1H, CH$_a$H$_b$ (Tyr)), 1.48 (m, J=6.8 Hz, 2H, CH$_2$CH$_2$N (C$_{16}$H$_{33}$)), 1.31 (m, 26H, (CH$_2$)$_{13}$), 0.93 (t, J=6.1 Hz, 3H, CH$_3$). $^{31}$P NMR (202 MHz, CD$_3$OD): δ 15.44. ESI-MS: m/z calcd 659.39 (M+H)$^+$. found 660.8 (M+H)$^+$.

O-[({[(2R)-1-(2,6-diamino-9H-purin-9-yl)propan-2-yl]oxy}methyl)(hydroxy)phosphoryl]-N-octyl-L-tyrosinamide (15a)

$^1$H NMR (500 MHz, CD$_3$OD): δ 7.99 (s, 1H, CH of DAP), 7.28 (d, J=8.3 Hz, 2H, aromatic), 7.15 (d, J=8.8 Hz, 2H, aromatic), 4.33 (dd, J=14.7, 2.9 Hz, 1H) and 4.18 (dd, J=14.6, 6.3 Hz, 1H) (CHO and $CH_aH_bP$), 4.06-4.01 (m, 3H, $CH_2N$ and $CHNH_2$ (Tyr)), 3.87 (dd, J=13.7, 9.3 Hz, 1H, $CH_aH_bP$), 3.28-3.13 (m, 3H, $CH_aH_b$ (Tyr) and $CH_2N$ ($C_8H_{17}$)), 3.07 (dd, J=14.2, 7.4 Hz, 1H, $CH_aH_b$ (Tyr)), 1.47 (m, J=7.4 Hz, 2H, $CH_2CH_2N$ ($C_8H_{17}$)), 1.32 (m, 10H, $(CH_2)_5$), 1.24 (d, J=6.3 Hz, 3H, $CH_3$—CH), 0.93 (t, J=6.9 Hz, 3H, $CH_3$). $^{31}P$ NMR (202 MHz, $CD_3OD$): δ 15.42. ESI-MS: m/z calcd 576.29 $(M+H)^+$. found 577.4 $(M+H)^+$.

REFERENCES

The following publications are incorporated by reference herein in their entireties:
1. De Clercq, E., The acyclic nucleoside phosphonates from inception to clinical use: historical perspective. *Antiviral Res.* 2007, 75, 1-13.
2. Clercq, E. D.; Holy, A.; Rosenberg, I.; Sakuma, T.; Balzarini, J.; Maudgal, P. C., A novel selective broad-spectrum anti-DNA virus agent. *Nature* 1986, 323, 464-467.
3. Clercq, E. D.; Sakuma, T.; Baba, M.; Pauwels, R.; Balzarini, J.; Rosenberg, I.; Holý, A., Antiviral activity of phosphonylmethoxyalkyl derivatives of purine and pyrimidines. *Antiviral Res.* 1987, 8, 261-272.
4. Cundy, K. C.; Bidgood, A. M.; Lynch, G.; Shaw, J. P.; Griffin, L.; Lee, W. A., Pharmacokinetics, bioavailability, metabolism, and tissue distribution of cidofovir (HPMPC) and cyclic HPMPC in rats. *Drug Metab. Dispos.* 1996, 24, 745-752.
5. Cundy K C, L. Z., Hitchcock M J, Lee W A., Pharmacokinetics of cidofovir in monkeys. Evidence for a prolonged elimination phase representing phosphorylated drug. *Drug Metab. Dispos.* 1996, 24, 738-44.
6. Bijsterbosch, M. K.; Smeijsters, L. J. J. W.; van Berkel, T. J. C., Disposition of the Acyclic Nucleoside Phosphonate (S)-9(3-Hydroxy-2-Phosphonylmethoxypropyl)Adenine. *Antimicrob. Agents Chemother.* 1998, 42, 1146-1150.
7. Peterson, L. W.; McKenna, C. E., Prodrug approaches to improving the oral absorption of antiviral nucleotide analogues. *Expert Opinion on Drug Delivery* 2009, 6, 405-420.
8. Eriksson, U.; Peterson, L. W.; Kashemirov, B. A.; Hilfinger, J. M.; Drach, J. C.; Borysko, K. Z.; Breitenbach, J. M.; Kim, J. S.; Mitchell, S.; Kijek, P.; McKenna, C. E., Serine Peptide Phosphoester Prodrugs of Cyclic Cidofovir: Synthesis, Transport, and Antiviral Activity. *Mol. Pharm.* 2008, 5, 598-609.
9. Grimm, J. B.; Wilson, K. J.; Witter, D. J., Suppression of racemization in the carbonylation of amino acid-derived aryl triflates. *Tetrahedron Lett.* 2007, 48, 4509-4513.
10. Turk, S. R.; Shipman, C., Jr.; Nassiri, R.; Genzlinger, G.; Krawczyk, S. H.; Townsend, L. B.; Drach, J. C. Pyrrolo[2,3-d]pyrimidine nucleosides as inhibitors of human cytomegalovirus. *Antimicrob. Agents Chemother.* 1987, 31, 544-550.
11. Prichard, M. N.; Turk, S. R.; Coleman, L. A.; Engelhardt, S. L.; Shipman, C., Jr.; Drach, J. C. A microtiter virus yield reduction assay for the evaluation of antiviral compounds against human cytomegalovirus and herpes simplex virus. *J. Virol. Methods* 1990, 28, 101-106.
12. Kern, E. R.; Hartline, C.; Harden, E.; Keith, K.; Rodriguez, N.; Beadle, J. R.; Hostetler, K. Y. Enhanced inhibition of orthopoxvirus replication in vitro by alkoxyalkyl esters of cidofovir and cyclic cidofovir. *Antimicrob. Agents Chemother.* 2002, 46, 991-995.
13. Goldstein, A. Biostatistics, an introductory text. Macmillan: New York, 1964, 272 pp.

What is claimed is:
1. A compound of the following formula (I) or (II), or a pharmaceutically acceptable salt thereof:

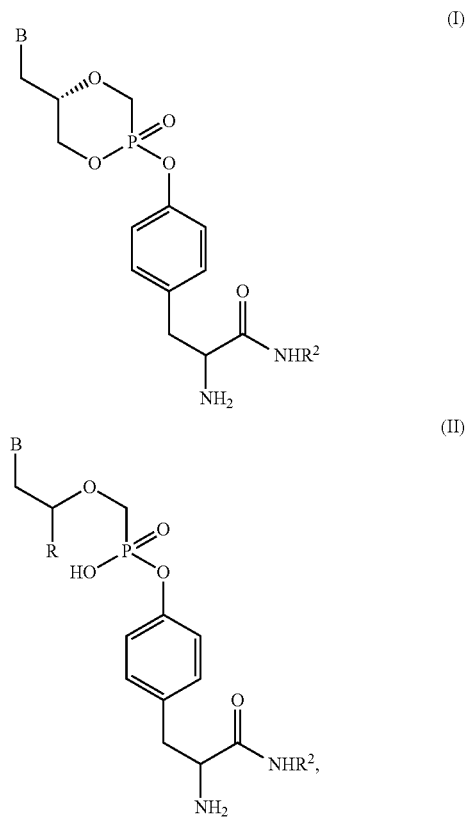

wherein B is 9 adeninyl, 1-cytosinyl, 9-guaninyl, 2,6-diamino-9-purinyl, 7-deaza-9-guaninyl, 8-aza-9-guaninyl or 2,4-diaminopyrimidine-6-oxidanyl, R is H, $CH_2OH$ or methyl, and $R^2$ is a $C_{12-18}$ alkyl group.

2. The compound of claim 1, wherein $R^2$ is a $C_{14-18}$ alkyl group.

3. The compound of claim 1, wherein $R^2$ is a $C_{16}$ alkyl group.

4. A compound of claim 1, wherein the compound is:
O-[(5S)-5-[(6-Amino-9H-purin-9-yl)methyl]-2-oxido-1,4,2-dioxaphosphinan-2-yl]-N-dodecyl-(L)-tyrosinamide ((L)-Tyr($NHC_{12}H_{25}$)—(S)-cHPMPA),
O-[(5S)-5-[(6-Amino-9H-purin-9-yl)methyl]-2-oxido-1,4,2-dioxaphosphinan-2-yl]-N-tetradecyl-(L)-tyrosinamide ((L)-Tyr ($NHC_{14}H_{29}$)—(S)-cHPMPA),
O-[(5S)-5-[(6-Amino-9H-purin-9-yl)methyl]-2-oxido-1,4,2-dioxaphosphinan-2-yl]-N-hexadecyl-(L)-tyrosinamide ((L)-Tyr ($NHC_{16}H_{33}$)—(S)-cHPMPA),
O-[(5S)-5-[(6-Amino-9H-purin-9-yl)methyl]-2-oxido-1,4,2-dioxaphosphinan-2-yl]-N-octadecyl-(L)-tyrosinamide ((L)-Tyr($NHC_{18}H_{37}$)—(S)-cHPMPA),
O-[([[(2S)-1-(6-Amino-9H-purin-9-yl)-3-hydroxypropan-2-yl]oxy]methyl)(hydroxy)-phosphoryl]-N-dodecyl-(L)-tyrosinamide ((L)-Tyr ($NHC_{12}H_{25}$)—(S)-HPMPA),
O-[([[(2S)-1-(6-Amino-9H-purin-9-yl)-3-hydroxypropan-2-yl]oxy]methyl)(hydroxy)-phosphoryl]-N-tetradecyl-(L)-tyrosinamide ((L)-Tyr ($NHC_{14}H_{29}$)—(S)-HPMPA), O-[([[(2S)-1-(6-Amino-9H-purin-9-yl)-3-hydroxypropan-2-yl]oxy]methyl)(hydroxy)-phosphoryl]-N-hexadecyl-(L)-tyrosinamide ((L)-Tyr (NHC$_{16}$H$_{33}$)—(S)-HPMPA), O-[([[(2S)-1-(6-Amino-9H-purin-9-yl)-3-hydroxypropan-2-yl]oxy]methyl)-(hydroxy)-phosphoryl]-N-octadecyl-(L)-tyrosinamide ((L)-Tyr (NHC$_{18}$H$_{37}$)—(S)-HPMPA), O-[(5S)-5-[(4-amino-2-oxopyrimidin-1 (2H)-yl)methyl]-2-oxido-1,4,2-dioxaphosphinan-2-yl]-N-hexadecyl-(L)-tyrosinamide ((L)-Tyr (NHC$_{16}$H$_{33}$)—(S)-cHPMPC);

O-[([[(2S)-1-(4-amino-2-oxopyrimidin-1(2H)-yl)-3-hydroxypropan-2-yl] oxy]methyl)-(hydroxy)phosphoryl]-N-hexadecyl-(L)-tyrosinamide ((L)-Tyr (NHC$_{16}$H$_{33}$)—(S)-HPMPC), or O-[{[2-(6-Amino-9H-purin-9-yl)ethoxy]methyl}(hydroxy)phosphoryl]-N-hexadecyl-L-tyrosinamide ((L)-Tyr (NHC$_{16}$H$_{33}$)-PMEA).

5. A pharmaceutical composition comprising a compound of claim 1, and a pharmaceutically acceptable carrier.

6. The pharmaceutical composition of claim 5, wherein R$^2$ is C$_{14-18}$ alkyl group.

7. The pharmaceutical composition of claim 5, wherein the compound is
(L)-Tyr(NHC$_{12}$H$_{25}$)—(S)-cHPMPA,
(L)-Tyr(NHC$_{14}$H$_{29}$)—(S)-cHPMPA,
(L)-Tyr(NHC$_{16}$H$_{33}$)—(S)-cHPMPA,
(L)-Tyr(NHC$_{18}$H$_{37}$)—(S)-cHPMPA,
(L)-Tyr(NHC$_{12}$H$_{25}$)—(S)-HPMPA,
(L)-Tyr(NHC$_{14}$H$_{29}$)—(S)-HPMPA,
(L)-Tyr(NHC$_{16}$H$_{33}$)—(S)-HPMPA,
(L)-Tyr(NHC$_{18}$H$_{37}$)—(S)-HPMPA,
((L)-Tyr(NHC$_{16}$H$_{33}$)—(S)-cHPMPC,
((L)-Tyr(NHC$_{16}$H$_{33}$)—(S)-HPMPC, or
(L)-Tyr (NHC$_{16}$H$_{33}$)-PMEA.

8. The pharmaceutical composition of claim 5, wherein R$^2$ is a C$_{16}$ alkyl group.

9. A method of inhibiting viral replication in a pox or herpes virus-infected cell in need thereof, comprising exposing the cell in culture to a compound of claim 1.

10. The method of claim 9, wherein R$^2$ is C$_{14-18}$ alkyl group.

11. The method of claim 9, wherein the compound is
(L)-Tyr(NHC$_{12}$H$_{25}$)—(S)-cHPMPA,
(L)-Tyr(NHC$_{14}$H$_{29}$)—(S)-cHPMPA,
(L)-Tyr(NHC$_{16}$H$_{33}$)—(S)-cHPMPA,
(L)-Tyr(NHC$_{18}$H$_{37}$)—(S)-cHPMPA,
(L)-Tyr(NHC$_{12}$H$_{25}$)—(S)-HPMPA,
(L)-Tyr(NHC$_{14}$H$_{29}$)—(S)-HPMPA,
(L)-Tyr(NHC$_{16}$H$_{33}$)—(S)-HPMPA,
(L)-Tyr(NHC$_{18}$H$_{37}$)—(S)-HPMPA,
((L)-Tyr (NHC$_{16}$H$_{33}$)—(S)-cHPMPC,
((L)-Tyr(NHC$_{16}$H$_{33}$)—(S)-HPMPC, or
(L)-Tyr (NHC$_{16}$H$_{33}$)-PMEA.

12. The method of claim 9, wherein R$^2$ is a C$_{16}$ alkyl group.

13. A method of treating a pox or herpes virus infection in an individual in need thereof, comprising administering to the individual a therapeutically effective amount of a compound of claim 1.

14. The method of claim 13, wherein R$^2$ is C$_{14-18}$ alkyl group.

15. The method of claim 13, wherein the compound is
(L)-Tyr(NHC$_{12}$H$_{25}$)—(S)-cHPMPA,
(L)-Tyr(NHC$_{14}$H$_{29}$)—(S)-cHPMPA,
(L)-Tyr(NHC$_{16}$H$_{33}$)—(S)-cHPMPA,
(L)-Tyr(NHC$_{18}$H$_{37}$)—(S)-cHPMPA,
(L)-Tyr(NHC$_{12}$H$_{25}$)—(S)-HPMPA,
(L)-Tyr(NHC$_{14}$H$_{29}$)—(S)-HPMPA,
(L)-Tyr(NHC$_{16}$H$_{33}$)—(S)-HPMPA,
(L)-Tyr(NHC$_{18}$H$_{37}$)—(S)-HPMPA,
((L)-Tyr(NHC$_{16}$H$_{33}$)—(S)-cHPMPC,
((L)-Tyr(NHC$_{16}$H$_{33}$)—(S)-HPMPC, or
(L)-Tyr (NHC$_{16}$H$_{33}$)-PMEA.

16. The method of claim 13, wherein R$^2$ is a C$_{16}$ alkyl group.

17. A method of preparing an amino acid conjugate of an acyclic nucleoside phosphonate, comprising
reacting an acyclic nucleoside phosphonate with EtOH in the presence of bromotripyrrolidinophosphonium hexafluorophosphate (PyBrOP) to produce a nucleoside phosphonate mono-ethyl ester of the formula

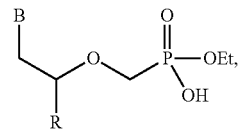

wherein B is a base and R is H or methyl;
coupling the nucleoside phosphonate mono-ethyl ester to a Boc-protected amino acid, said Boc-protected amino acid comprising a carboxamide group containing a C$_{6-20}$ alkyl moiety, to produce a Boc-protected nucleoside phosphonate di-ester of the formula

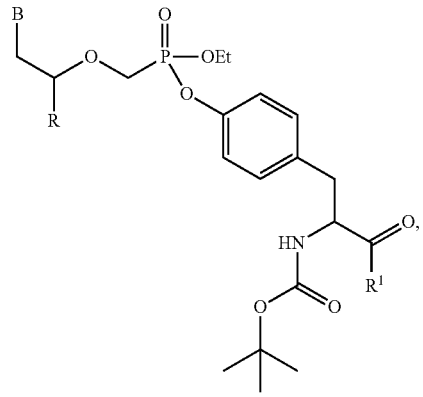

wherein R$^1$ is NHC$_n$H$_{(2n+1)}$, wherein n=6-20; and
deethylating and deprotecting the Boc-protected nucleoside phosphonate di-ester to produce an acyclic nucleoside phosphonate analogue of the formula

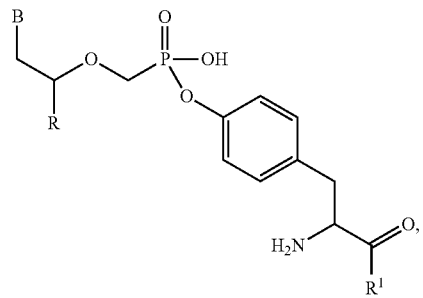

wherein B is 9-adeninyl, 1-cytosinyl, 9-guaninyl, 2,6-diamino-9-purinyl, 7-deaza-9-guaninyl, 8-aza-9-guaninyl or 2,4-diaminopyrimidine-6-oxidanyl.

18. The method of claim 17, wherein B is 9-adeninyl or 2,6-diamino-9-purinyl.

\* \* \* \* \*

UNITED STATES PATENT AND TRADEMARK OFFICE
CERTIFICATE OF CORRECTION

PATENT NO. : 9,550,803 B2
APPLICATION NO. : 14/114827
DATED : January 24, 2017
INVENTOR(S) : Charles E. McKenna et al.

Page 1 of 1

It is certified that error appears in the above-identified patent and that said Letters Patent is hereby corrected as shown below:

In the Specification

Column 1, Line 17:
After "STATEMENT REGARDING FEDERALLY SPONSORED RESEARCH OR DEVELOPMENT", Delete:
"This invention was made with Government support under Grant Nos. R43AI091216 and R44AI056864 from the National Institutes of Health. The Government has certain rights in this invention."

And Insert:
--This invention was made with government support under R43 AI091216, and R44 AI056864 awarded by the National Institutes of Health. The government has certain rights in the invention.--

Signed and Sealed this
Tenth Day of June, 2025

Coke Morgan Stewart
*Acting Director of the United States Patent and Trademark Office*